US007816473B2

(12) United States Patent
Hays et al.

(10) Patent No.: US 7,816,473 B2
(45) Date of Patent: Oct. 19, 2010

(54) DIACETYLENIC MATERIALS FOR SENSING APPLICATIONS

(75) Inventors: David S. Hays, Woodbury, MN (US); Ryan B. Prince, Woodbury, MN (US); G. Marco Bommarito, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/177,643

(22) Filed: Jul. 8, 2005

(65) Prior Publication Data

US 2005/0245712 A1 Nov. 3, 2005

Related U.S. Application Data

(62) Division of application No. 10/325,276, filed on Dec. 19, 2002, now Pat. No. 6,963,007.

(51) Int. Cl.
C08F 38/00 (2006.01)
C07C 253/00 (2006.01)
C07C 255/00 (2006.01)
(52) U.S. Cl. ........................ 526/285; 558/333; 558/405
(58) Field of Classification Search ................. 526/285; 558/333, 405
See application file for complete search history.

(56) References Cited

U.S. PATENT DOCUMENTS

| | | | |
|---|---|---|---|
| 3,709,860 A | 1/1973 | Fischer et al. ............... 260/77.5 |
| 3,999,946 A | 12/1976 | Patel et al. ..................... 23/253 |
| 4,189,399 A | 2/1980 | Patel ........................... 252/408 |
| 4,195,058 A | 3/1980 | Patel ........................... 422/56 |
| 4,215,208 A | 7/1980 | Yee et al. ..................... 526/285 |
| 4,228,126 A | 10/1980 | Patel et al. .................... 422/56 |
| 4,235,108 A | 11/1980 | Patel ........................... 73/356 |
| 4,238,352 A | 12/1980 | Patel ........................... 252/408 |
| 4,299,917 A | 11/1981 | Berger et al. .................. 435/19 |
| 4,339,240 A | 7/1982 | Patel ........................... 23/230 |
| 4,389,217 A | 6/1983 | Baughman et al. ............. 436/2 |
| 4,434,235 A | 2/1984 | Rabi et al. ................... 436/110 |
| 4,721,769 A | 1/1988 | Rubner ........................ 528/75 |
| 4,735,745 A | 4/1988 | Preziosi et al. ............... 252/408 |
| 4,767,826 A | 8/1988 | Liang et al. .................. 525/421 |
| 4,849,500 A | 7/1989 | Rubner ........................ 528/345 |
| 4,916,211 A | 4/1990 | Rubner ........................ 528/480 |
| 5,156,810 A | 10/1992 | Ribi ........................... 422/82 |
| 5,491,097 A | 2/1996 | Ribi et al. .................... 436/518 |
| 5,571,568 A | 11/1996 | Ribi et al. .................... 427/487 |
| 5,618,735 A | 4/1997 | Saul et al. .................... 436/518 |
| 5,622,872 A | 4/1997 | Ribi ........................... 436/518 |
| 5,660,993 A | 8/1997 | Cathey et al. ................. 435/7.9 |
| 5,672,465 A | 9/1997 | Patel et al. .................... 430/332 |
| 5,685,641 A | 11/1997 | Ribi ........................... 374/162 |
| 5,753,517 A | 5/1998 | Brooks et al. |
| 5,798,215 A | 8/1998 | Cathey et al. ................. 435/7.9 |
| 5,918,981 A * | 7/1999 | Ribi ........................... 374/162 |
| 5,951,993 A | 9/1999 | Scholz et al. |
| 6,011,556 A | 1/2000 | Narita et al. ................... 435/5 |
| 6,046,455 A | 4/2000 | Ribi et al. .................... 250/372 |
| 6,080,423 A | 6/2000 | Charych et al. ............... 424/450 |
| 6,103,217 A | 8/2000 | Charych ....................... 424/321 |
| 6,156,524 A | 12/2000 | Fournier et al. .............. 435/7.33 |
| 6,183,772 B1 | 2/2001 | Charych et al. ............... 424/450 |
| 6,277,652 B1 | 8/2001 | Jo et al. ...................... 436/518 |
| 6,299,897 B1 | 10/2001 | Nagy et al. .................. 424/443 |
| 6,306,598 B1 | 10/2001 | Charych et al. ................ 435/6 |
| 6,361,962 B1 | 3/2002 | Lentini et al. ................. 435/29 |
| 6,375,871 B1 | 4/2002 | Bentsen et al. ............... 264/1.6 |
| 6,387,614 B1 | 5/2002 | Cheng et al. ................... 435/4 |
| 6,395,561 B1 | 5/2002 | Charych et al. ............... 436/501 |
| 6,420,622 B1 | 7/2002 | Johnston et al. ............... 602/41 |
| 6,451,191 B1 | 9/2002 | Bentsen et al. ............... 204/600 |
| 6,500,646 B1 | 12/2002 | Kuriyama et al. .............. 435/69 |
| 6,607,744 B1 | 8/2003 | Ribi ........................... 424/439 |
| 6,963,007 B2 | 11/2005 | Hays et al. ................... 558/333 |
| 2001/0046451 A1 | 11/2001 | Patel .......................... 422/58 |
| 2002/0137233 A1 | 9/2002 | Stevens et al. ............... 436/531 |
| 2003/0129618 A1 | 7/2003 | Moronne et al. ................ 435/6 |
| 2004/0126897 A1* | 7/2004 | Prince et al. ................. 436/518 |
| 2004/0132217 A1 | 7/2004 | Prince et al. ................. 436/518 |
| 2005/0101794 A1 | 5/2005 | Hays et al. |
| 2005/0153370 A1 | 7/2005 | Lakshmi et al. |
| 2006/0041057 A1 | 2/2006 | Koecher et al. ............... 525/50 |
| 2006/0041099 A1 | 2/2006 | Cernohous et al. ............ 528/44 |
| 2006/0134796 A1 | 6/2006 | Bommarito et al. ......... 436/166 |

FOREIGN PATENT DOCUMENTS

| | | |
|---|---|---|
| DE | 36 13 492 | 10/1987 |
| EP | 0 532 430 A1 | 7/1992 |
| EP | 0 926 497 A2 | 6/1999 |

(Continued)

OTHER PUBLICATIONS

Bader et al.; "Membrane-spanning Symmetric and Asymmetric Diyne Amphiphiles"; Faraday Discuss. Chem. Soc., 1986, 81, 329-337.

(Continued)

Primary Examiner—William K Cheung

(57) ABSTRACT

Diacetylenic materials for the colorimetric detection of an analyte or exposure to certain environmental factors are disclosed as well as the polymerization reaction products of these diacetylenic compounds.

31 Claims, No Drawings

FOREIGN PATENT DOCUMENTS

| GB | 1 361 577 | | 7/1974 |
|---|---|---|---|
| GB | 1 463 434 | | 2/1977 |
| JP | 56-147807 | | 11/1981 |
| JP | 63-130135 | | 6/1988 |
| JP | 4-69358 | * | 3/1992 |
| JP | 11-28099 | | 2/1999 |
| WO | WO 96/21885 | * | 7/1996 |
| WO | WO 99/10743 A1 | | 3/1999 |
| WO | WO 01/71317 A1 | | 9/2001 |
| WO | WO 02/00920 A2 | | 1/2002 |
| WO | WO 02/079486 | | 10/2002 |
| WO | WO 02/082086 | | 10/2002 |

OTHER PUBLICATIONS

Pan et al. "Molecular Recognition and Colorimetric Detection of Cholera Toxin in Poly(diacetylene) Liposomes Incorporating $G_{m1}$ Ganglioside"; Langmuir 1997, 13, pp. 1365-1367 (1997 American Chemical Society).

Ma et al. "Colorimetric Detection of *Escherichia coli* by Polydiacetylene Vesicles Functionalized with Glycolipid"; J. Am. Chem. Soc. 1998, 120; pp. 12678-12679 (1998 American Chemical Society).

Budilova, I. et al.; "Reaction of Diynoyl Chlorides with Para-Substituted Phenols"; J. Org. Chem. USSR. vol. 26; 1990; pp. 264-267.

Gusev B.P. et al.; "Chemistry of Polyenic and Polyacetylenic Compounds Communication 6. New Method for the Synthesis of Butadiyne Derivatives"; Bull. Acad. Sci. USSR Div. Chem. Sci. 1962; pp. 1000-1005.

Besace, Y. et al.; "Reaction de Delepine en serie acetylenique"; Bulletin De La Societe Chimique De France; 1971, No. 4; pp. 1468-1472 (no translation sent).

Besace, Y. et al.; "Synthese des amines primaries α-diacetyleniques par la methode de Delepine"; C.R. Acad. Sc. Paris, t.270 (May 11, 1970); pp. 1605-1607 (no translation sent).

Rodriguez-Abad, R. et al.; "Unsymmetrically Substituted Aliphatic Diacetylenes Containing Amine Functionalities"; Synthetic Communications, 28(23), pp. 4333-4338 (1998).

Gusev, B.P. et al.; "Chemistry of Polyenic and Polyynic Compounds Communication 13. Synthesis of Dialkylamino Derivatives of 1,3-Diynes"; Bull. Acad. Sci. USSR Div. Chem. Sci.; 1965; pp. 820-823.

Gusev, B.P. et al.; "Chemistry of Polyenic and Polyynic Compounds Communication 18. Diacetylenic Amines"; Bull. Acad. Sci. USSR Div. Chem. Sci.; 1996; pp. 1163-1166.

Singh, A. et al.; "Self-assembled Microstructures from a Polymerizable Ammonium Surfactant: Di(Hexacosa-12,14-diynyl)dimethylammonium Bromide"; J. Chem. Soc. Chem. Commun., 1988; pp. 1222-1223.

Schulze, K. et al.; "Zum Mechanismus Der Umlagerung Beim Alkalischen Abbau Der Quartaren Salze Von 1-Dialkylaminoalkadinen-(2,4)"; Tetrahedron, vol. 31, pp. 1455-1459; 1975 (no translation sent).

Cannon, J. et al.; "1,6-Diammonium-2,4-hexadiyne Analogs of Hexamethonium"; Journal of Medicinal Chemistry, 1974, vol. 17, No. 3, pp. 355-358.

Mino et al.; "Photoreactivity of 10,12-Pentacosadiynoic Acid Monolayrs and Color Transitions of the Polymerized Monolayers on an Aqueous Subphase"; Langmuir, 1992, vol. 8, 594-598.

Chance et al.; "Thermal effects on the optical properties of single crystals and solution-cast films of urethane substituted polydiacetylenes"; J. Chem. Phys.; vol. 71(1) Jul. 1, 1979; pp. 206-211.

Shibata, M.; "Reversible Colour Phase Transitions and Annealing Properties of Langmuir-Blodgett Polydiacetylene Films"; Thin Solid Films; vol. 179 (1989) pp. 433-437.

Kaneko et al.; "Absorption properties and structure changes caused by pre-annealing in polydiacetylene Langmuir-Blodgett films"; Thin Solid Films; vol. 210/211 (1992) pp. 548-550.

A. Ulman; "An Introduction to Ultrathin Organic Films" 1991 pp. 237-304.

A. Ulman; "An Introduction to Ultrathin Organic Films" 1991 pp. 101-236.

A. Ulman; "An Introduction to Ultrathin Organic Films" 1991 pp. 48-58.

Abrams et al.; "Triple Bond Isomerizations: 2- to 9-Decyn-1-ol"; Organic Syntheses; vol. 66, 1988 pp. 127-131.

Brandsma, L.; Preparative Acetylenic Chemistry; 1971 (cover and copyrights pages).

Alcaraz et al.; "Synthesis and Properties of Photoactivatable Phospholipid Derivatives Designed to Probe the Membrane-Associate Domains of Proteins"; J. Org. Chem.; vol. 61; 1996 pp. 192-201.

Wu, S.; "Polymer Interface and Adhesion" 1982; pp. 169-198, 613-618.

Millar et al; "Synthesis of Z,Z-Skipped Diene Macrolide Pheromones for Cryptolestes and Oryzaephilus Grain Beetles (*Coleoptera cucujidae*)" J. Org. Chem.; vol. 49, 1984; pp. 2332-2338.

Mohanty et al.; "A highly sensitive fluorescent micro-assay of $H_2O_2$ release from activated human leukocytes using a dihydroxyphenoxazine derivative"; Journal of Immunological Methods; vol. 202 (1997) pp. 133-141.

Kolusheva et al.; "A colorimetric assay for rapid screening of antimicrobial peptides"; Nature Biotechnology; vol. 18, Feb. 2000 pp. 225-227.

Kolusheva et al.; "Rapid Colorimetric Detection of Antibody-Epitope Recognition at a Biomimetic Membrane Interface"; J. Am. Chem. Soc.; vol. 123; 2001; pp. 417-422.

Kolusheva et al.; "Peptide-Membrane Interactions Studied by a New Phospholipid/Polydiacetylene Colorimetric Vesicle Assay"; Biochemistry; vol. 39; 2000; pp. 15851-15859.

Xu et al.; "Synthesis of Photopolymerizable Long-Chain Conjugated Diacetylenic Acids and Alcohols from Butadiyne Synthons"; J. Org. Chem.; vol. 56; 1991; pp. 7183-7186.

Bell et al; "The total synthesis of a technetium chelate—tamoxifen complex"; Can. J. Chem. vol. 77; 1999; pp. 146-154.

Khoobehi, B.et al.; "Fluorescent Labeling of Blood Cells for Evaluation of Retinal and Choroidal Circulation"; Ophthalmic Surgery and Lasers; vol. 30; No. 2; Feb. 1999; pp. 140-145.

Hupfer, B. et al.; "Spreading and Polymerization Behavior of Diacetylenic Phospholipids at the Gas-Water Interface"; Chemistry and Physics of Lipids; vol. 33; 1983; pp. 263-282.

J. Israelachvili; "Intermolecular and Surface Forces" (2nd Ed.); Academic Press, New York (1992) pp. 340-435.

Koshkina et al.; "Synthesis of New Amphiphilic Bifunctional Diynes Modified in the Hydrophilic and Hydrophobic Parts*"; Russian Journal of Organic Chemistry; vol. 30; No. 9; 1994; p. 1345-1351.

Ohba et al.; "Synthesis of Novel Amphiphilic Diacetylenes with Amino or Ammonium Functionality"; Tetrahedron, vol. 47, No. 47, p. 9947-9952, 1991.

Alami et al.; "A Convenient Route to Unsymmetrical Conjugated Diynes"; Tetrahedron Letters, vol. 37, No. 16, p. 2763-2766, 1996.

Baughman, R.H. et al.; "Raman spectral shifts relevant to electron delocalization in polydiacetylenes"; The Journal of Chemical Physics; vol. 60, No. 12, Jun. 15, 1974; p. 4755-4759.

Dumont, J. et al.; "Amines et aminoacides polyacetyleniques"; C.R. Acad. Sc. Paris, t260 (Jan. 4, 1965). Groupe 8. p. 215-217 (no. translation sent).

Dumont, J. et al.; "Contribution a l'etude des amines ω-acetyleniques vrais et de leurs derives"; Bulletin De La Societe Chimique De France; 1967 No. 2; p. 588-596 (no translation sent).

Kosuge, H. et al.; "Polydiacetylenes in Organic-Inorganic Hybrid Systems"; Mol. Cryst. Liq. Cryst., vol. 377, p. 13-18; 2002.

Rubner, M.F.; "Synthesis and Characterization of Polyurethane-Diacetylene Segmented Copolymers"; Macromolecules 1986, vol. 19, p. 2114-2128.

Rubner, M.F.; "Novel Optical Properties of Polyurethane-Diacetylene Segmented Copolymers"; Macromolecules 1986; vol. 19, p. 2129-2138.

Nallicheri, R.A. et al.; "Thermal and Mechanical Properties of Polyurethane-Diacetylene Segmented Copolymers. 1. Molecular Weight and Annealing Effects"; Macromolecules 1990; vol. 23, p. 1005-1016.

Nallicheri, R.A. et al.; "Thermal and Mechanical Properties of Polyurethane-Diacetylene Segmented Copolymers. 2. Effects of Diacetylene Cross-Polymerization"; Macromolecules 1990; vol. 23, p. 1017-1025.

Hammond, P.T. et al.; "Thermochromism in Liquid Crystaline Polydiacetylenes"; Macromolecules 1997; vol. 30, p. 5773-5782.

Siemsen, P. et al.; "Acetylenic Coupling: A Powerful Tool in Molecular Construction"; Angewandte Chemie International Edition; 2000; vol. 39 (15); p. 2632-2657.

Charych, D. et al.; "A 'litmus test' for molecular recognition using artificial membranes"; Chemistry & Biology; 1996; vol. 3, No. 2; pp. 113-120.

Alekseev, A. et al.; "Polymerization of Diacetylenic Alcohol and Its Mixtures with a Diacetylenic Acid in Langmuir-Blodgett Films"; Russian Journal of Physical Chemistry; vol. 76, No. 5, 2002; pp. 796-801.

STN search of p. 1 and 2: Alekseev et al. Document No. 137:248029; Russian Journal of Physical Chemistry; Abstract of U document cited in U of 892, (2002).

Andersson, K, et al.; "Predicting the kinetics of peptide-antibody interactions using a multivariate experimental design of sequence and chemical space"; Journal of Molecular Recognition; 2001; vol. 14, pp. 62-71.

Cheng, Q. et al.; "Amino Acid Terminated Polydiacetylene Lipid Microstructures: Morphology and Chromatic Transition"; Langmuir; 2000, vol. 16, pp. 5333-5342.

Valverde, C.; "Some Novel Photosensitive Diacetylene Diurethanes and Their Mixtures in Common Polymers"; Polymers for Advanced Technologies; vol. 7, 1996; pp. 27-30.

M. Paulsson et al.; "Adhesion of Staphylococci to Chemically Modified and Native Polymers, and the Influence of Preadsorbed Fibronectin, Vitronectin and Fibrinogen"; *Biomaterials*; 1993, vol. 14, No. 11: pp. 845-853.

A. Warnes; Development of an enzyme-linked immunosorbent assay for staphylococcal protein A produced in *Escherichia coli* by pUC8 based plasmids containing the *Staphylococcus aureus* Cowan I protein A gene; Journal of Immunological Methods, 93 (1986); pp. 63-70.

D. Low; "Issues in Identification and Susceptibility Testing, The staphylococci in Human Disease"; Clinical Microbiology; 1997; pp. 233-252.

J. Israelachvili et al.; "Physical priciples of membrane organization"; Quarterly Reviews of Biophysics 13, 2 (1980) pp. 121-200.

M. Starzak; The Physical Chemistry of Membranes; Department of Chemistry; 1984; pp. 1-24.

S. Oellerich et al.; "Peripheral and Integral Binding of Cytochrome c to Phospholipids Vesicles"; Journal of Physical Chemistry B.; 2004; 108; pp. 3871-1878.

M. Zuckermann et al.; "Insertion and Pore Formation Driven by Adsorption of Proteins Onto Lipid Bilayer Membrane-Water Interfaces"; Biophysical Journal; vol. 81; Nov. 2001; pp. 2458-2472.

M. Shibata et al.; "Reversible Colour Phase Transitions and Annealing Properties of Langmuir-Blodgett Polydiacetylene Films"; Thin Solid Films; 179 (1989) pp. 433-437.

A. S. Alekseev et al.; "Polymerization of a Diacetylenic Alcohol and its Mixtures with a Diacetylenic Acid in Langmuir-Blodgett Films"; Russian Journal of Physical Chemistry, vol. 76, No. 5, 2002 pp. 796-801.

D. Charych et al.; "A Litmus Test for Molecular Recognition Using Artificial Membranes"; Current Biology Ltd.; Chemistry & Biology, Feb. 1996, 3: pp. 113-120.

* cited by examiner

DIACETYLENIC MATERIALS FOR SENSING APPLICATIONS

CROSS-REFERENCE TO RELATED APPLICATIONS

This application is a division of U.S. patent application Ser. No. 10/325,276, filed Dec. 19, 2002 now U.S. Pat. No. 6,963,007.

FIELD OF THE INVENTION

This invention relates to diacetylenic materials for the colorimetric detection of an analyte or exposure to certain environmental factors. In addition, the invention relates to the polymerization reaction products of at least one of the diacetylenic compounds disclosed herein.

BACKGROUND OF THE INVENTION

Various circumstances require that exposure to certain environmental factors, such as heat and ultraviolet (UV) light be monitored and recorded. For example, the need to know whether a product has been exposed either to an undesirable time-temperature history, which results in substantial degradation, or to a correct time-temperature history required during processing is frequently required. This applies, for example, to frozen foods, pharmaceuticals or photographic films that may be exposed to undesirable high temperatures for significant time periods during storage and distribution. Additionally, exposure to the ultraviolet radiation of sunlight can cause rapid aging and hardening of the skin and can cause DNA damage, which can lead to skin cancer or other cellular proliferative diseases.

Diacetylenes are typically colorless and undergo addition polymerization, either thermally or by actinic radiation. As the polymerization proceeds, these compounds undergo a contrasting color change to blue or purple. Utilization of this class of compounds is known for use as time-temperature history indicators, thermochromic indicating materials and as radiation-dosage indicators.

Efforts continue, however, to make sensing devices employing diacetylenes more accurate, more tailored to a given application, less complex and more available to non-technical personnel in a wide variety of environments. Devices, which can be conveniently transported and used individually for a particular application then discarded, are particularly desirable.

SUMMARY OF THE INVENTION

The present invention relates to compounds of the formula

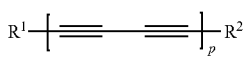

where $R^1$ is

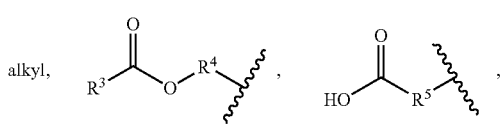

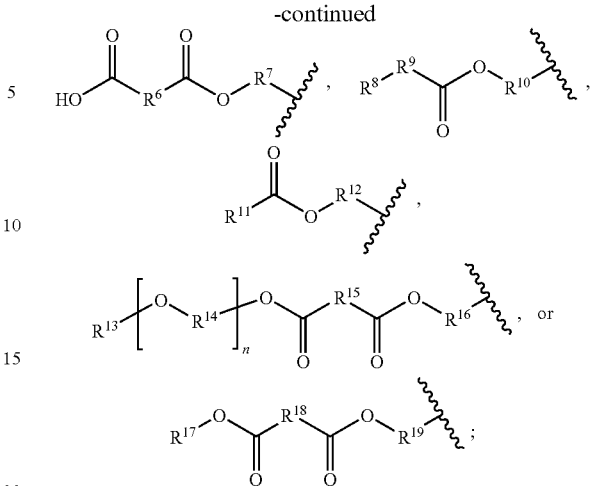

$R^2$ is

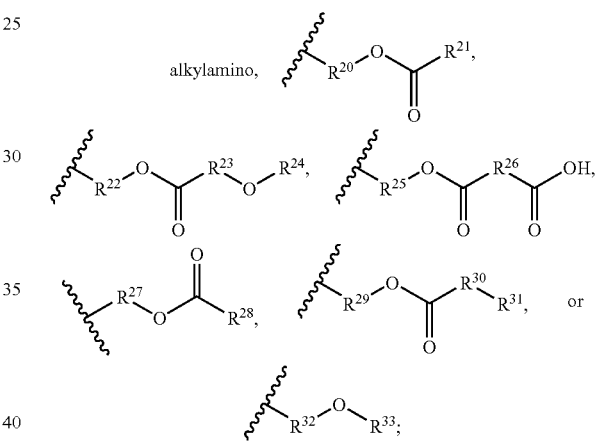

$R^3$, $R^8$, $R^{13}$, $R^{24}$, $R^{31}$ and $R^{33}$ are independently alkyl; $R^4$, $R^5$, $R^7$, $R^{14}$, $R^{16}$, $R^{19}$, $R^{20}$, $R^{22}$, $R^{25}$, and $R^{32}$ are independently alkylene; $R^6$, $R^{15}$, $R^{18}$, and $R^{26}$ are independently alkylene, alkenylene, or arylene; $R^9$ is alkylene or —$NR^{34}$—; $R^{10}$, $R^{12}$, $R^{27}$, and $R^{29}$ are independently alkylene or alkylene-arylene; $R^{11}$ and $R^{28}$ are independently alkynyl; $R^{17}$ is 2,5-dioxo-1-pyrrolidinyl; $R^{21}$ is alkylamino or alkyl; $R^{23}$ is arylene; $R^{30}$ is alkylene or —$NR^{36}$—; $R^{34}$, and $R^{36}$ are independently H or $C_1$-$C_4$ alkyl; p is 1-5; and n is 1-20; and where $R^1$ and $R^2$ are not the same.

Also provided is a method for the detection of electromagnetic radiation in the ultraviolet range of the electromagnetic spectrum comprising contacting at least one compound described above with electromagnetic radiation in the ultraviolet range of the electromagnetic spectrum and observing a color change.

Also provided is a polymerized composition including the polymerization reaction product of at least one compound described above.

Also provided is a method for the detection of thermal radiation including contacting a polymerized composition described above with thermal radiation and observing a color change.

The above summary of the present invention is not intended to describe each disclosed embodiment or every implementation of the present invention. The detailed description that follows more particularly exemplifies these embodiments.

DETAILED DESCRIPTION

The present invention provides for diacetylenic materials. In particular, the present invention is directed to diacetylenic materials for the colorimetric detection of an analyte or exposure to certain environmental factors. While the present invention is not so limited, an appreciation of various aspects of the invention will be gained through a discussion of the examples provided below.

All numbers are herein assumed to be modified by the term "about."

The recitation of numerical ranges by endpoints includes all numbers subsumed within that range (e.g. 1 to 5 includes 1, 1.5, 2, 2.75, 3, 3.80, 4, and 5).

For the following defined terms, these definitions shall be applied, unless a different definition is given in the claims or elsewhere in this specification.

As used herein, the term "alkyl" refers to a straight or branched chain or cyclic monovalent hydrocarbon radical having a specified number of carbon atoms. Alkyl groups include those with one to twenty carbon atoms. Examples of "alkyl" as used herein include, but are not limited to, methyl, ethyl, n-propyl, n-butyl, n-pentyl, isobutyl, and isopropyl, and the like. It is to be understood that where cyclic moieties are intended, at least three carbons in said alkyl must be present. Such cyclic moieties include cyclopropyl, cyclobutyl, cyclopentyl, cyclohexyl and cycloheptyl.

As used herein, the term "alkylene" refers to a straight or branched chain or cyclic divalent hydrocarbon radical having a specified number of carbon atoms. Alkylene groups include those with one to fourteen carbon atoms. Examples of "alkylene" as used herein include, but are not limited to, methylene, ethylene, trimethylene, tetramethylene and the like. It is to be understood that where cyclic moieties are intended, at least three carbons in said alkylene must be present. Such cyclic moieties include cyclopropylene, cyclobutylene, cyclopentylene, cyclohexylene and cycloheptylene.

As used herein, the term "alkenylene" refers to a straight or branched chain or cyclic divalent hydrocarbon radical having a specified number of carbon atoms and one or more carbon-carbon double bonds. Alkenylene groups include those with two to eight carbon atoms. Examples of "alkenylene" as used herein include, but are not limited to, ethene-1,2-diyl, propene-1,3-diyl, and the like.

As used herein, the term "arylene" refers to divalent unsaturated aromatic carboxylic radicals having a single ring, such as phenylene, or multiple condensed rings, such as naphthylene or anthrylene. Arylene groups include those with six to thirteen carbon atoms. Examples of "arylene" as used herein include, but are not limited to, benzene-1,2-diyl, benzene-1,3-diyl, benzene-1,4-diyl, naphthalene-1,8-diyl, and the like.

As used herein, the term "alkylene-arylene", refers to an alkylene moiety as defined above bonded to an arylene moiety as defined above. Examples of "alkylene-arylene" as used herein include, but are not limited to, —$CH_2$-phenylene, —$CH_2CH_2$-phenylene, and —$CH_2CH_2CH_2$-phenylene.

As used herein, the term "alkynyl" refers to a straight or branched chain or cyclic monovalent hydrocarbon radical having from two to thirty carbons and at least one carbon-carbon triple bond. Examples of "alkynyl" as used herein include, but are not limited to, ethynyl, propynyl and butynyl.

As used herein, the term "alkylamino" means alkyl group defined as above bonded to a primary, secondary or tertiary amino group, or salts thereof. Examples of "alkylamino" as used herein include, but are not limited to, —$(CH_2)_{1-15}$—$NH_3$, and —$(CH_2)_{1-15}$—$N(CH_3)_3$.

The present invention provides compounds of the formula

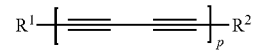

where $R^1$ is

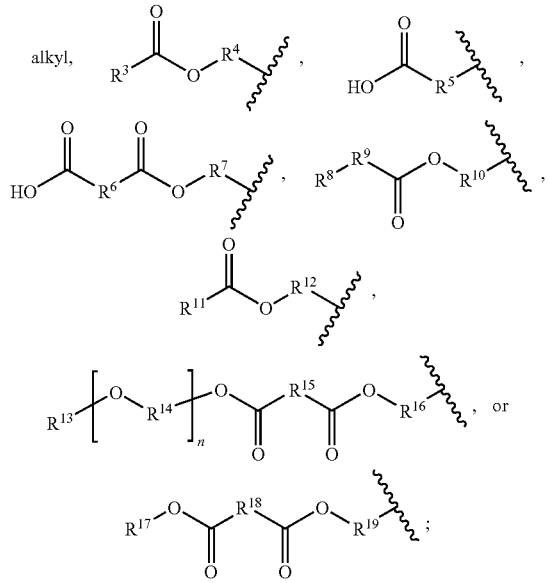

$R^2$ is

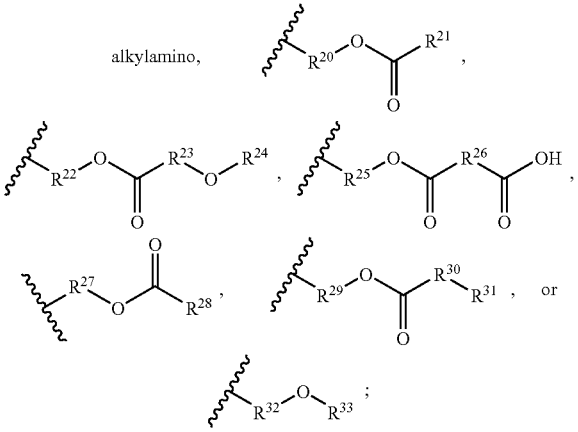

$R^3$, $R^8$, $R^{13}R^{24}$, $R^{31}$ and $R^{33}$ are independently alkyl; $R^4$, $R^5$, $R^7$, $R^{14}$, $R^{16}$, $R^{19}$, $R^{20}$, $R^{22}$, $R^{25}$, and $R^{32}$ are independently alkylene; $R^6$, $R^{15}$, $R^{18}$, and $R^{26}$ are independently alkylene, alkenylene, or arylene; $R^9$ is alkylene or —$NR^{34}$—; $R^{10}$, $R^{12}$, $R^{27}$, and $R^{29}$ are independently alkylene or alkylene-arylene; $R^{11}$ and $R^{28}$ are independently alkynyl; $R^{17}$ is 2,5-dioxo-1-pyrrolidinyl; $R^{21}$ is alkylamino or alkyl; $R^{23}$ is arylene; $R^{30}$ is alkylene or —$NR^{36}$—; $R^{34}$, and $R^{36}$ are independently H or $C_1$-$C_4$ alkyl; p is 1-5; and n is 1-20; and where $R^1$ and $R^2$ are not the same.

Examples of $R^1$ when $R^1$ is alkyl include $C_1$-$C_{20}$ alkyl, $C_6$-$C_{18}$ alkyl, and $C_{12}$-$C_{16}$ alkyl. Additional examples of $R^1$ when $R^1$ is alkyl include dodecyl and hexadecyl.

Examples of $R^2$ when $R^2$ is alkylamino include $C_1$-$C_{20}$ alkylamino, $C_6$-$C_{18}$ alkylamino, and $C_{11}$-$C_{16}$ alkylamino. Additional examples of $R^2$ when $R^2$ is alkylamino include $(C_1$-$C_{18}$ alkyl)-$NR^{35}{}_3 X$, where $R^{35}$ is H or $C_1$-$C_4$ alkyl, such as methyl, for example, and X is a suitable counterion, such as $F^-$, $Br^-$, $Cl^-$, $I^-$, $OH^-$, $N_3^-$, $HCO_3^-$, or $CN^-$, for example. Further examples of $R^2$ when $R^2$ is alkylamino include —$(CH_2)_{11}$—$NH_3 X$, where X is defined as above, —$(CH_2)_{11}$—$N(CH_3)_3 X$, where X is defined above, —$(CH_2)_{15}$—$N(CH_3)_3 X$, where X is defined above, and —$(CH_2)_{15}$—$NH_3 X$, where X is defined above.

Examples of $R^3$ include $C_1$-$C_{20}$ alkyl, and $C_6$-$C_{18}$ alkyl. Additional examples of $R^3$ include undecyl and pentadecyl.

Examples of $R^4$ include $C_1$-$C_{14}$ alkylene, and $C_1$-$C_4$ alkylene. Additional examples of $R^4$ include methylene (—$CH_2$—), trimethylene, (—$CH_2 CH_2 CH_2$—), and tetramethylene (—$CH_2 CH_2 CH_2 CH_2$—).

Examples of $R^5$ include $C_1$-$C_{14}$ alkylene, and $C_1$-$C_3$ alkylene. Additional examples of $R^5$ include ethylene (—$CH_2 CH_2$—), and trimethylene (—$CH_2 CH_2 CH_2$—).

Examples of $R^6$ when $R^6$ is alkylene include $C_1$-$C_{14}$ alkylene, and $C_1$-$C_3$ alkylene. Additional examples of $R^6$ when $R^6$ is alkylene include ethylene (—$CH_2 CH_2$—), and trimethylene (—$CH_2 CH_2 CH_2$—). Examples of $R^6$ when $R^6$ is alkenylene include $C_2$-$C_8$ alkenylene, and $C_2$-$C_4$ alkenylene. An additional example of $R^6$ when $R^6$ is alkenylene includes ethenylene (—C=C—). Examples of $R^6$ when $R^6$ is arylene include $C_6$-$C_{13}$ arylene, and phenylene. An additional example of $R^6$ when $R^6$ is arylene is benzene-1,2-diyl.

Examples of $R^7$ include $C_1$-$C_{14}$ alkylene, and $C_2$-$C_9$ alkylene. Additional examples of $R^7$ include ethylene (—$CH_2 CH_2$—), trimethylene (—$CH_2 CH_2 CH_2$—), tetramethylene (—$CH_2 CH_2 CH_2 CH_2$—), pentamethylene (—$CH_2 CH_2 CH_2 CH_2 CH_2$—), hexamethylene (—$CH_2 CH_2 CH_2 CH_2 CH_2 CH_2$—), heptamethylene (—$CH_2 CH_2 CH_2 CH_2 CH_2 CH_2 CH_2$—), octamethylene (—$CH_2 CH_2 CH_2 CH_2 CH_2 CH_2 CH_2 CH_2$—), and nonamethylene (—$CH_2 CH_2 CH_2 CH_2 CH_2 CH_2 CH_2 CH_2 CH_2$—).

Examples of $R^8$ include $C_1$-$C_{16}$ alkyl, and $C_1$-$C_8$ alkyl. Additional examples of $R^8$ include butyl, pentyl and hexyl.

$R^9$ is independently alkylene or —$NR^{34}$—, where $R^{34}$ is H or $C_1$-$C_4$ alkyl.

Examples of $R^9$ when $R^9$ is alkylene include $C_1$-$C_{14}$ alkylene, and $C_1$-$C_3$ alkylene, such as methylene (—$CH_2$—) for example. Examples of $R^9$ when $R^9$ is —$NR^{34}$— include —NH—, —N($CH_2 CH_3$)—, and —N($CH_3$)—.

Examples of $R^{10}$ when $R^{10}$ is alkylene include $C_1$-$C_{14}$ alkylene, and $C_1$-$C_8$ alkylene. Additional examples of $R^{10}$ when $R^{10}$ is alkylene include methylene (—$CH_2$—), ethylene (—$CH_2 CH_2$—), trimethylene (—$CH_2 CH_2 CH_2$—), tetramethylene (—$CH_2 CH_2 CH_2 CH_2$—), —C($CH_3$)$_2$—, and —CH(($CH_2$)$_{1-4}CH_3$)—. Examples of $R^{10}$ when $R^{10}$ is alkylene-arylene include ($C_1$-$C_{14}$ alkylene)-arylene, and ($C_1$-$C_{14}$ alkylene)-phenylene. An additional example of $R^{10}$ when $R^{10}$ is alkylene-arylene includes —$CH_2$-phenylene.

Examples of $R^{11}$ include $C_2$-$C_{30}$ alkynyl, and $C_{20}$-$C_{25}$ alkynyl. Additional examples of $R^{11}$ include $C_2$-$C_{30}$ alkynyl having at least two carbon-carbon triple bonds (—C≡C—), and $C_{20}$-$C_{25}$ alkynyl having at least two carbon-carbon triple bonds. Further examples of $R^{11}$ include $C_{22}$ alkynyl having at least two carbon-carbon triple bonds, $C_{24}$ alkynyl having at least two carbon-carbon triple bonds. Yet further examples of $R^{11}$ include —$(CH_2)_8$—C≡C—C≡C—$(CH_2)_9 CH_3$, and —$(CH_2)_8$—C≡C—C≡C—$(CH_2)_{11} CH_3$.

Examples of $R^{12}$ when $R^{12}$ is alkylene include $C_1$-$C_{14}$ alkylene, and $C_1$-$C_8$ alkylene. Additional examples of $R^{12}$ when $R^{12}$ is alkylene include methylene (—$CH_2$—), ethylene (—$CH_2 CH_2$—), trimethylene (—$CH_2 CH_2 CH_2$—), tetramethylene (—$CH_2 CH_2 CH_2 CH_2$—), —C($CH_3$)$_2$—, and —CH(($CH_2$)$_{1-4}CH_3$)—. Examples of $R^{12}$ when $R^{12}$ is alkylene-arylene include ($C_1$-$C_{14}$ alkylene)-arylene, and ($C_1$-$C_{14}$ alkylene)-phenylene. An additional example of $R^{12}$ when $R^{12}$ is alkylene-arylene includes —$CH_2$-phenylene.

Examples of $R^{13}$ include $C_1$-$C_4$ alkyl, such as methyl for example.

Examples of $R^{14}$ include $C_1$-$C_4$ alkylene, such as ethylene (—$CH_2 CH_2$—) for example.

Examples of $R^{15}$ when $R^{15}$ is alkylene include $C_1$-$C_{14}$ alkylene, and $C_1$-$C_3$ alkylene. Additional examples of $R^{15}$ when $R^{15}$ is alkylene include ethylene (—$CH_2 CH_2$—), and trimethylene (—$CH_2 CH_2 CH_2$—). Examples of $R^{15}$ when $R^{15}$ is alkenylene include $C_2$-$C_8$ alkenylene, and $C_2$-$C_4$ alkenylene. An additional example of $R^{15}$ when $R^{15}$ is alkenylene includes ethenylene (—C=C—). Examples of $R^{15}$ when $R^{15}$ is arylene include $C_6$-$C_{13}$ arylene, and phenylene. An additional example of $R^{15}$ when $R^{15}$ is arylene is benzene-1,4-diyl.

Examples of $R^{16}$ include $C_1$-$C_{14}$ alkylene, and $C_2$-$C_9$ alkylene. Additional examples of $R^{16}$ include ethylene (—$CH_2 CH_2$—), trimethylene (—$CH_2 CH_2 CH_2$—), tetramethylene (—$CH_2 CH_2 CH_2 CH_2$—), pentamethylene (—$CH_2 CH_2 CH_2 CH_2 CH_2$—), hexamethylene (—$CH_2 CH_2 CH_2 CH_2 CH_2 CH_2$—), heptamethylene (—$CH_2 CH_2 CH_2 CH_2 CH_2 CH_2 CH_2$—), octamethylene (—$CH_2 CH_2 CH_2 CH_2 CH_2 CH_2 CH_2 CH_2$—), and nonamethylene (—$CH_2 CH_2 CH_2 CH_2 CH_2 CH_2 CH_2 CH_2 CH_2$—).

Examples of $R^{17}$ include groups that activate the neighboring ester group toward acyl transfer. Such ester activating groups include pentafluorophenol, pentachlorophenol, 2,4,6-trichlorophenol, 3-nitrophenol, N-hydroxysuccinimide, N-hydroxyphthalimide and those disclosed in M. Bodanszky, "Principles of Peptide Synthesis," (Springer-Verlag, 1984), for example. An additional example of $R^{17}$ is 2,5-dioxo-1-pyrrolidinyl.

Examples of $R^{18}$ when $R^{18}$ is alkylene include $C_1$-$C_{14}$ alkylene, and $C_1$-$C_3$ alkylene. Additional examples of $R^{18}$ when $R^{18}$ is alkylene include ethylene (—$CH_2 CH_2$—), and trimethylene (—$CH_2 CH_2 CH_2$—). Examples of $R^{18}$ when $R^{18}$ is alkenylene include $C_2$-$C_8$ alkenylene, and $C_2$-$C_4$ alkenylene. An additional example of $R^{18}$ when $R^{18}$ is alkenylene includes ethenylene (—C=C—). Examples of $R^{18}$ when $R^{18}$ is arylene include $C_6$-$C_{13}$ arylene, and phenylene. An additional example of $R^{18}$ when $R^{18}$ is arylene is benzene-1,2-diyl.

Examples of $R^{19}$ include $C_1$-$C_{14}$ alkylene, and $C_2$-$C_9$ alkylene. Additional examples of $R^{19}$ include ethylene (—$CH_2 CH_2$—), trimethylene (—$CH_2 CH_2 CH_2$—), tetramethylene (—$CH_2 CH_2 CH_2 CH_2$—), pentamethylene (—$CH_2 CH_2 CH_2 CH_2 CH_2$—), hexamethylene (—$CH_2 CH_2 CH_2 CH_2 CH_2 CH_2$—), heptamethylene (—$CH_2 CH_2 CH_2 CH_2 CH_2 CH_2 CH_2$—), octamethylene (—$CH_2 CH_2 CH_2 CH_2 CH_2 CH_2 CH_2 CH_2$—), and nonamethylene (—$CH_2 CH_2 CH_2 CH_2 CH_2 CH_2 CH_2 CH_2 CH_2$—).

Examples of $R^{20}$ include $C_1$-$C_{14}$ alkylene, $C_1$-$C_9$ alkylene, and $C_1$-$C_4$ alkylene. Additional examples of $R^{20}$ include methylene (—$CH_2$—), ethylene (—$CH_2 CH_2$—), trimethylene (—$CH_2 CH_2 CH_2$—), tetramethylene (—$CH_2 CH_2 CH_2 CH_2$—), pentamethylene (—$CH_2 CH_2 CH_2 CH_2 CH_2$—), hexamethylene (—$CH_2 CH_2 CH_2 CH_2 CH_2 CH_2$—), heptamethylene (—$CH_2 CH_2 CH_2 CH_2 CH_2 CH_2$—), octamethylene ($-CH_2CH_2CH_2CH_2CH_2CH_2CH_2CH_2-$), and nonamethylene ($-CH_2CH_2CH_2CH_2CH_2CH_2CH_2CH_2CH_2-$).

Examples of $R^{21}$ when $R^{21}$ is alkylamino include $C_1$-$C_{20}$ alkylamino, $C_6$-$C_{18}$ alkylamino, and $C_{11}$-$C_{16}$ alkylamino. Additional examples of $R^{21}$ when $R^{21}$ is alkylamino include ($C_1$-$C_{18}$ alkyl)—$NR^{35}{}_3X$, where $R^{35}$ is H or $C_1$-$C_4$ alkyl, such as methyl, for example, and X is a suitable counterion, such as $F^-$, $Br_-$, $Cl^-$, $I^-$, $OH^-$, $N_3^-$, $HCO_3^-$, and $CN^-$, for example. Further examples of $R^{21}$ when $R^{21}$ is alkylamino include $-(CH_2)_{10}-NH_3X$, where X is defined as above, $-(CH_2)_{10}-N(CH_3)_3X$, where X is defined above, $-(CH_2)_{14}-N(CH_3)_3X$, where X is defined above, and $-(CH_2)_{14}-NH_3X$, where X is defined above. Examples of $R^{21}$ when $R^{21}$ is alkyl include $C_1$-$C_{20}$ alkyl, $C_6$-$C_{18}$ alkyl, and $C_{10}$-$C_{17}$ alkyl. Additional examples of $R^{21}$ when $R^{21}$ is alkyl include decyl, undecyl, tridecyl, tetradecyl, pentadecyl, heptadecyl.

Examples of $R^{22}$ include $C_1$-$C_{14}$ alkylene, and $C_2$-$C_9$ alkylene. Additional examples of $R^{22}$ include ethylene ($-CH_2CH_2-$), trimethylene ($-CH_2CH_2CH_2-$), and tetramethylene.

Examples of $R^{23}$ include $C_6$-$C_{13}$ arylene, and phenylene. An additional example of $R^{23}$ when $R^{23}$ is arylene is benzene-1,4-diyl.

Examples of $R^{24}$ include $C_1$-$C_{20}$ alkyl, and $C_6$-$C_{18}$ alkyl. Additional examples of $R^{24}$ include methyl, ethyl, propyl, butyl, pentyl, hexyl, heptyl, octyl, nonyl, and dodecyl.

Examples of $R^{25}$ include $C_1$-$C_{14}$ alkylene, and $C_2$-$C_9$ alkylene. Additional examples of $R^{25}$ include ethylene ($-CH_2CH_2-$), trimethylene ($-CH_2CH_2CH_2-$), tetramethylene ($-CH_2CH_2\ CH_2CH_2-$), pentamethylene ($-CH_2CH_2CH_2CH_2CH_2-$), hexamethylene ($-CH_2CH_2CH_2\ CH_2CH_2CH_2-$), heptamethylene ($-CH_2CH_2CH_2CH_2CH_2CH_2-$), octamethylene ($-CH_2CH_2CH_2CH_2CH_2CH_2CH_2CH_2-$), and nonamethylene ($-CH_2CH_2CH_2CH_2CH_2CH_2CH_2CH_2CH_2-$).

Examples of $R^{26}$ when $R^{26}$ is alkylene include $C_1$-$C_{14}$ alkylene, and $C_1$-$C_3$ alkylene. Additional examples of $R^{26}$ when $R^{26}$ is alkylene include ethylene ($-CH_2CH_2-$), and trimethylene ($-CH_2CH_2CH_2-$). Examples of $R^{26}$ when $R^{26}$ is alkenylene include $C_2$-$C_8$ alkenylene, and $C_2$-$C_4$ alkenylene. An additional example of $R^{26}$ when $R^{26}$ is alkenylene includes ethenylene ($-C=C-$). Examples of $R^{26}$ when $R^{26}$ is arylene include $C_6$-$C_{13}$ arylene, and phenylene. An additional example of $R^{26}$ when $R^{26}$ is arylene is benzene-1,2-diyl.

Examples of $R^{27}$ when $R^{27}$ is alkylene include $C_1$-$C_{14}$ alkylene, and $C_1$-$C_8$ alkylene. Additional examples of $R^{27}$ when $R^{27}$ is alkylene include methylene ($-CH_2-$), ethylene ($-CH_2CH_2-$), trimethylene ($-CH_2CH_2CH_2-$), tetramethylene ($-CH_2CH_2\ CH_2CH_2-$), $-C(CH_3)_2-$, and $-CH((CH_2)_{1-4}CH_3)-$. Examples of $R^{27}$ when $R^{27}$ is alkylene-arylene include ($C_1$-$C_{14}$ alkylene)-arylene, and ($C_1$-$C_{14}$ alkylene)-phenylene. An additional example of $R^{27}$ when $R^{27}$ is alkylene-arylene includes $-CH_2$-phenylene.

Examples of $R^{28}$ include $C_2$-$C_{30}$ alkynyl, and $C_{20}$-$C_{25}$ alkynyl. Additional examples of $R^{28}$ include $C_2$-$C_{30}$ alkynyl having at least two carbon-carbon triple bonds ($-C\equiv C-$), and $C_{20}$-$C_{25}$ alkynyl having at least two carbon-carbon triple bonds. Further examples of $R^{28}$ include $C_{22}$ alkynyl having at least two carbon-carbon triple bonds, $C_{24}$ alkynyl having at least two carbon-carbon triple bonds. Yet further examples of $R^{28}$ include $-(CH_2)_8-C\equiv C-C\equiv C-(CH_2)_9CH_3$, and $-(CH_2)_8-C\equiv C-C\equiv C-(CH_2)_{11}CH_3$.

Examples of $R^{29}$ when $R^{29}$ is alkylene include $C_1$-$C_{14}$ alkylene, and $C_1$-$C_8$ alkylene. Additional examples of $R^{29}$ when $R^{29}$ is alkylene include methylene ($-CH_2-$), ethylene ($-CH_2CH_2-$), trimethylene ($-CH_2CH_2CH_2-$), tetramethylene ($-CH_2CH_2\ CH_2CH_2-$), $-C(CH_3)_2-$, and $-CH((CH_2)_{1-4}CH_3)-$. Examples of $R^{29}$ when $R^{29}$ is alkylene-arylene include ($C_1$-$C_{14}$ alkylene)-arylene, and ($C_1$-$C_{14}$ alkylene)-phenylene. An additional example of $R^{29}$ when $R^{29}$ is alkylene-arylene includes $-CH_2$-phenylene.

$R^{30}$ is independently alkylene or $-NR^{36}-$, where $R^{36}$ is H or $C_1$-$C_4$ alkyl.

Examples of $R^{30}$ when $R^{30}$ is alkylene include $C_1$-$C_{14}$ alkylene, and $C_1$-$C_3$ alkylene, such as methylene ($-CH_2-$) for example. Examples of $R^{30}$ when $R^{30}$ is $-NR^{36}-$ include $-NH$, $-N(CH_2CH_3)-$, and $-N(CH_3)-$.

Examples of $R^{31}$ include $C_1$-$C_{16}$ alkyl, and $C_1$-$C_8$ alkyl. Additional examples of $R^{31}$ include butyl, pentyl and hexyl.

Examples of $R^{32}$ include $C_1$-$C_{14}$ alkylene, and $C_2$-$C_9$ alkylene. Additional examples of $R^{32}$ include ethylene ($-CH_2CH_2-$), trimethylene ($-CH_2CH_2CH_2-$), tetramethylene ($-CH_2CH_2\ CH_2CH_2-$), pentamethylene ($-CH_2CH_2CH_2CH_2CH_2-$), and hexamethylene ($-CH_2CH_2CH_2\ CH_2CH_2CH_2-$).

Examples of $R^{33}$ include $C_1$-$C_{20}$ alkyl, $C_6$-$C_{18}$ alkyl, and $C_{10}$-$C_{16}$ alkyl. Additional examples of $R^{33}$ include dodecyl, tetradecyl, hexadecyl, and octadecyl.

Compounds of the present invention also include those where p can be 1 or 2 and n can be 1-20, 3-17, 6-14, or 9-11.

The invention is inclusive of the compounds described herein including isomers, such as structural isomers and geometric isomers, salts, solvates, polymorphs and the like.

The synthesis of the diacetylenic materials disclosed herein are adapted form published procedures such as those in Xu, Z.; Byun, H. S.; Bittman, R.; *J. Org. Chem.*, 1991, 56, 7183-7186. For example, the diacetylenes the formula I can be prepared as shown in Scheme 1 where n is typically 1 to 14. Compounds of the formula I can be prepared from compounds of the formula II via anion exchange with an anion exchange resin, such as "Dowex" anion exchange resin (available from Aldrich Chemical, Milwaukee, Wis.) for example, and a suitable eluent, such as aqueous sodium chloride for example.

Scheme 1:

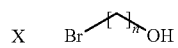

↓

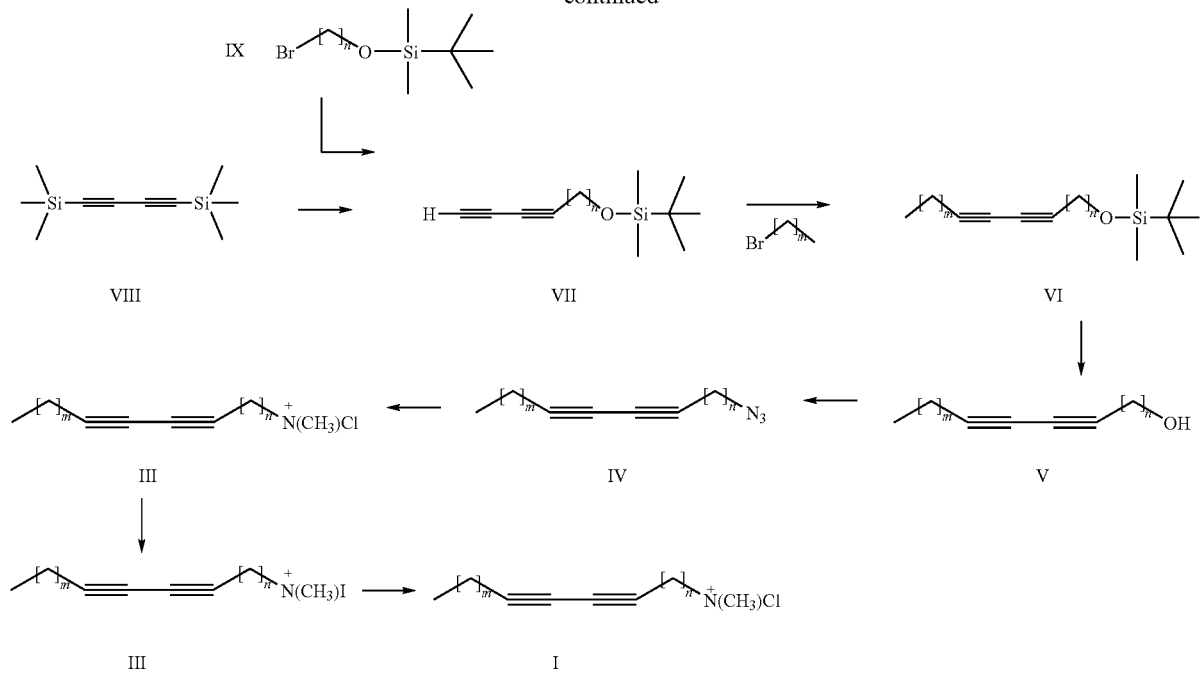

Compounds of formula II can be prepared from compounds of formula III by reaction with an appropriate alkylating agent in a suitable solvent. Suitable methylating agents include methyl iodide for example and suitable solvents include acetonitrile. The aforesaid reaction is run for a period of time from 1 hour to 96 hours, generally 20 hours, at a temperature from 20° C. to 70° C., generally from 20° C. to 50° C., in the presence of a base such as sodium carbonate for example.

Compounds of formula III can be prepared from compounds of formula IV by reaction with an appropriate reducing agent in a suitable solvent followed by protonation via a suitable acid to afford the salt. Suitable reducing agents include lithium aluminum hydride, sodium borohydride, and triphenylphosphine, for example. Suitable solvents include ether, tetrahydrofuran, dichloromethane, chloroform, and mixtures of these solvents with water, for example. Suitable acids include mineral acids such as HCl for example. The aforesaid reaction is run for a period of time from 1 hour to 96 hours, generally 20 hours, at a temperature from 0° C. to 40° C., generally from 10° C. to 25° C.

Compounds of formula IV can be prepared from compounds of formula VI via compounds of formula V. A compound of formula VI is reacted with a reagent suitable for the desilylation of a protected hydroxyl group in the presence of a suitable solvent. Such deprotecting reagents include tetrabutylammonium fluoride and those described in Greene and Wuts, "Protecting Groups in Organic Synthesis," (John Wiley & Son Press, 2nd Ed), for example. Suitable solvents include ether, tetrahydrofuran, dichloromethane, and chloroform, for example. The aforesaid reaction is run for a period of time from 0.5 hours to 5 hours, generally 1 hour, at a temperature from 0° C. to 40° C., generally from 10° C. to 25° C. The unpurified deprotected alcohol V is then reacted with a sulfonyl halide in the presence of a solvent. Suitable sulfonyl halides include methanesulfonyl chloride or p-toluenesulfonyl chloride. The aforesaid reaction is typically run for a period of time from 0.5 hours to 5 hours, generally 2 hours, at a temperature from 0° C. to 40° C., generally from 10° C. to 25° C., in the presence of a base such as trialkylamine or pyridine base. The resulting unpurified sulfonyl derivative is then reacted with sodium azide in a suitable solvent such as DMF. The aforesaid reaction is typically run for a period of time from 1 hour to 48 hours, generally 20 hours, at a temperature from 20° C. to 100° C., generally from 70° C. to 90° C., in the presence of a base such as trialkylamine or pyridine base.

Compounds of formula VI can be prepared from compounds of formula VII by reaction with a suitable alkyl halide or alkyl tosylate in a suitable solvent. Useful haloalkanes include primary alkyl halides such as 1-bromooctane, 1-bromododecane or 1-bromohexadecane. Suitable solvents include tetrahydrofuran, dichloromethane, and chloroform, for example. The aforesaid reaction is typically run for a period of time from 0.5 hours to 48 hours, generally 1 hour, at a temperature from −78° C. to 40° C., generally from −78° C. to −50° C., in the presence of a base such as an alkyl lithium base for example.

Compounds of formula VII can be prepared from compounds of formula VIII by reaction with a base such as an alkyl lithium base in a suitable solvent. Suitable alkyl lithium bases include methyl lithium. Suitable solvents include tetrahydrofuran, dichloromethane, and ether, for example. The aforesaid reaction is typically run for a period of time from 0.5 hours to 48 hours, generally 1 hour, at a temperature from −78° C. to 40° C., generally from −78° C. to −50° C. The resulting reaction mixture is then added to a solution of a suitable silyl protected hydroxy alkyl halide, such as those of formula IX for example, in a suitable solvent. Suitable solvents include tetrahydrofuran, dichloromethane, and chloroform, for example. The aforesaid reaction is typically run for a period of time from 0.5 hours to 48 hours, generally 1 hour, at a temperature from −78° C. to 40° C., generally from −20° C. to 0° C. The resulting compound was then reacted with tetrabutylammonium fluoride in a suitable solvent. Suitable solvents include tetrahydrofuran, dichloromethane, and chloroform, for example. The aforesaid reaction is typically run for a period of time from 0.5 hours to 48 hours, generally 20 hours, at a temperature from −78° C. to 40° C., generally from 0° C. to 25° C.

Silyl protected hydroxy alkyl halides, such as those of formula IX can be purchased commercially or prepared by reacting a suitable haloalcohol, such as those of formula X for example, with TBDMSCl in a suitable solvent. Suitable solvents include tetrahydrofuran, dichloromethane, and chloroform, for example. The aforesaid reaction is typically run for a period of time from 0.5 hours to 48 hours, generally 1 hour, at a temperature from 0° C. to 40° C., generally from 10° C. to 25° C., in the presence of a base such as imidazole for example.

Diacetylenes of the Formula XVII can be prepared as outlined in Scheme 2 where n is typically 10 to 14, m is typically 1 to 4, and p is typically 10-14.

suitable solvent. Suitable compounds of formula XIII include any azido functionalized acid chloride that affords the desired product such as 11-azidoundecanoyl chloride for example. Suitable acid chlorides include any acid chloride that affords the desired product such as 1-undecanoyl chloride and 1-pentadecanoyl chloride for example. Suitable solvents include ether, tetrahydrofuran, dichloromethane, and chloroform, for example. The aforesaid reaction is typically run for a period of time from 1 hour to 24 hours, generally 3 hours, at a temperature from 0° C. to 40° C., generally from 0° C. to 25° C., in the presence of a base such as trialkylamine or pyridine base.

Compounds of formula XV can be prepared via oxidative coupling of compounds of formula XIV by reaction with copper(I) chloride in the presence of a suitable solvent. Suitable solvents include alcohols such as methyl alcohol for example. The aforesaid reaction is typically run for a period of time from 24 hour to 72 hours, generally 48 hours, at a

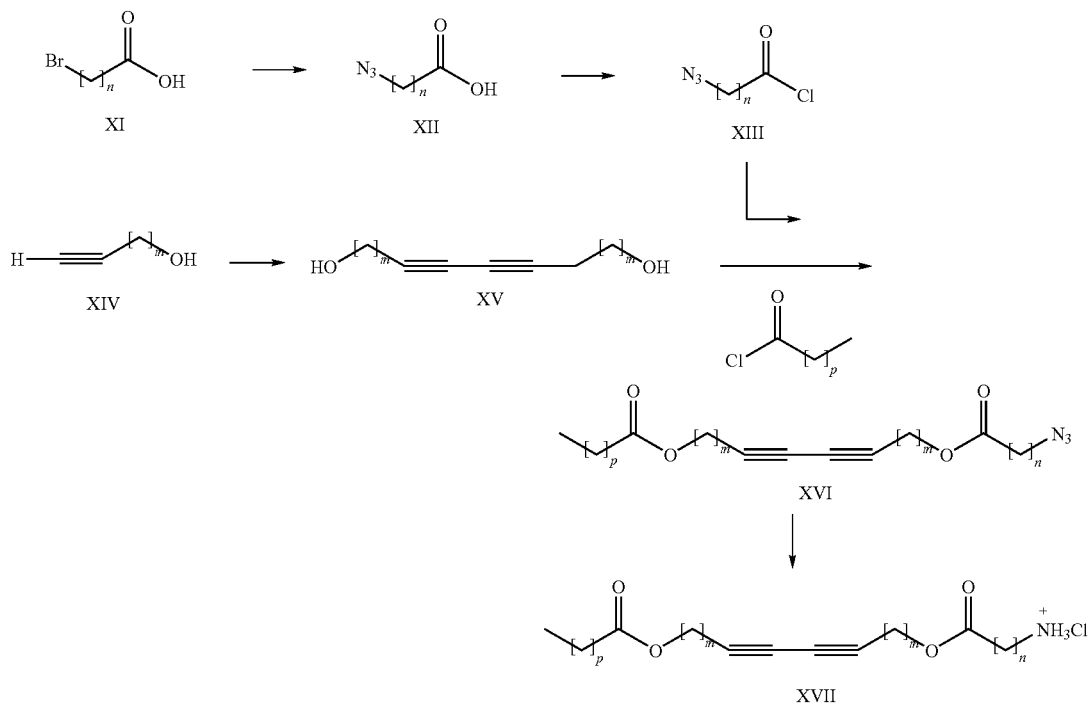

Compounds of formula XVII can be prepared from compounds of formula XVI by reaction with an appropriate reducing agent in a suitable solvent followed by protonation via a suitable acid to afford the salt. Suitable reducing agents include lithium aluminum hydride, sodium borohydride, and triphenylphosphine, for example. Suitable solvents include ether, tetrahydrofuran, dichloromethane, chloroform, and mixtures of these solvents with water, for example. Suitable acids include mineral acids such as HCl for example. The aforesaid reaction is run for a period of time from 1 hour to 96 hours, generally 20 hours, at a temperature from 0° C. to 40° C., generally from 10° C. to 25° C.

Compounds of formula XVI can be prepared from compounds of formula XV by reaction with a compound of formula XIII and a suitable acid chloride in the presence of a temperature from 0° C. to 40° C., generally from 0° C. to 25° C., in the presence of oxygen and a base such as pyridine.

Compounds of formula XIII can be prepared from compounds of formula XI via compounds of the formula XII as outlined in the Canadian Journal of Chemistry, 1999, 146-154. For example commercially available halogen derivatized carboxylic acids of the formula XI are reacted with sodium azide in the presence of a suitable solvent such as DMF. The aforesaid reaction is typically run for a period of time from 1 hour to 48 hours, generally 20 hours, at a temperature from 20° C. to 100° C., generally from 70° C. to 90° C. The unpurified azido derivatized carboxylic acid is then reacted with oxalyl chloride in the presence of a suitable solvent such as benzene for example. The aforesaid reaction is typically run for a period of time from 1 hour to 48 hours, generally 20 hours, at a temperature from 0° C. to 50° C., generally from 0° C. to 25° C.

Diacetylenes of the Formula XXIII can be prepared as outlined in Scheme 3 where n is typically 1 to 4 and m is typically 10 to 14.

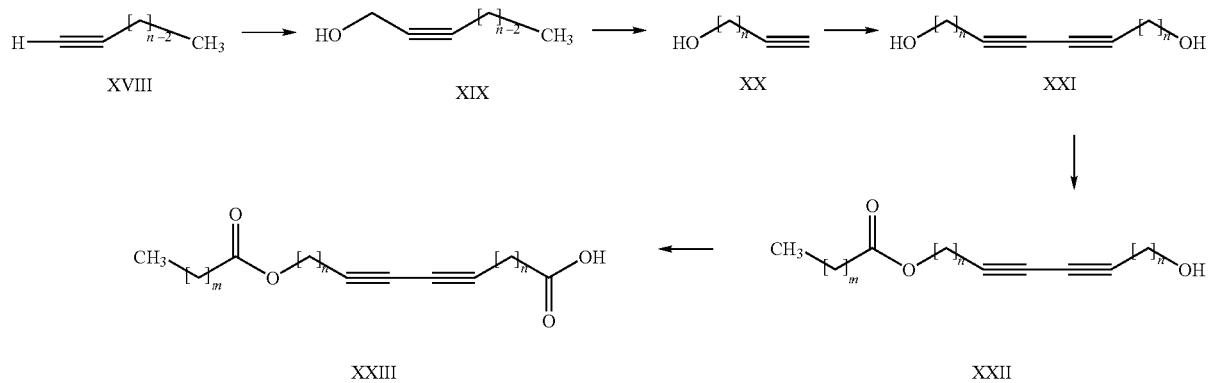

Scheme 3:

Compounds of formula XXIII can be prepared via oxidation from compounds of formula XXII by reaction with a suitable oxidizing agent in a suitable solvent such as DMF for example. Suitable oxidizing agents include Jones reagent and pyridinium dichromate for example. The aforesaid reaction is typically run for a period of time from 1 hour to 48 hours, generally 8 hours, at a temperature from 0° C. to 40° C., generally from 0° C. to 25° C.

Compounds of formula XXII can be prepared from compounds of formula XXI by reaction with a suitable acid chloride. Suitable acid chlorides include any acid chloride that affords the desired product such as lauroyl chloride, 1-dodecanoyl chloride, 1-tetradecanoyl chloride, 1-hexadecanoyl chloride, and 1-octadecanoyl chloride for example. Suitable solvents include ether, tetrahydrofuran, dichloromethane, and chloroform, for example. The aforesaid reaction is typically run for a period of time from 1 hour to 24 hours, generally 3 hours, at a temperature from 0° C. to 40° C., generally from 0° C. to 25° C., in the presence of a base such as trialkylamine or pyridine base.

Compounds of formula XXI are either commercially available (e.g. where n is 1-4) or can be prepared from compounds of the formula XVIII via compounds XIX and XX as outlined in Scheme 3 and disclosed in Abrams, Suzanne R.; Shaw, Angela C. "Triple-bond isomerizations: 2- to 9-decyn-1-ol," Org. Synth. (1988), 66 127-31 and Brandsma, L. "Preparative Acetylenic Chemistry," (Elsevier Pub. Co.: New York, 1971), for example.

Diacetylenic compounds as disclosed herein can also be prepared by reacting compounds of formula XXII with an anhydride such as succinic, glutaric, or phthalic anhydride in the presence of a suitable solvents such as toluene. The aforesaid reaction is typically run for a period of time from 1 hour to 24 hours, generally 15 hours, at a temperature from 50° C. to 125° C., generally from 100° C. to 125° C.

The diacetylenic compounds as disclosed herein self assemble in solution to form ordered assemblies that can be polymerized using any actinic radiation such as, for example, electromagnetic radiation in the UV or visible range of the electromagnetic spectrum. Polymerization of the diacetylenic compounds disclosed herein result in polymerization reaction products that have a color in the visible spectrum less than 570 nm, between 570 nm and 600 nm, or greater than 600 nm depending on their conformation and exposure to external factors. Typically, polymerization of the diacetylenic compounds disclosed herein result in meta-stable blue phase polymer networks that include a polydiacetylene backbone. These meta-stable blue phase polymer networks undergo a color change from bluish to reddish-orange upon exposure to external factors such as heat, a change in solvent or counterion, if available, or physical stress for example. Polymerization products of some of the diacetylenic compounds disclosed herein can exhibit a reversible color change and/or a three state color change. For example, after polymerization the resulting blue-phase polymer network can change color to a reddish-orange state upon exposure to heat, a change in solvent or counterion, or physical stress. This reddish-orange polymer network can then change color to a yellowish-orange state upon further exposure to heat, a change in solvent or counterion, or physical stress. Additionally, polymer networks disclosed herein can cycle between these reddish-orange and yellowish-orange states in a reversible manner.

The ability of the diacetylenic compounds and their polymerization products disclosed herein to undergo a visible color change upon exposure to a variety of elements, including ultraviolet light, physical stress, a change in solvent and a change in counter ion, for example, make them ideal candidates for the preparation of various sensing devices. Such sensing devices can employ the diacetylenic compounds and their polymerization products disclosed herein in solution or in their solid state. For example, the diacetylenic compounds and their polymerization products disclosed herein can be used as ultraviolet light dosimeters to measure exposure to ultraviolet radiation. The diacetylenic compounds disclosed herein respond to UV-A, UV-B, and UV-C light in a manner similar to the human skin, thereby closely matching the erythemal response. Thus, such dosimeters could serve as a warning to a user against excessive solar UV exposure.

The structural requirements of diacetylenic molecule for a given sensing application are typically application specific. Features such as overall chain length, solubility, polarity, crystallinity, and the presence of functional groups for further molecular modification all cooperatively determine a diacetylenic molecule's ability to serve as a useful sensing material.

The diacetylenic compounds disclosed herein possess the capabilities described above and can be easily and efficiently polymerized into networks that undergo the desired color changes in response to heat, a change in solvent or counterion, if available, or physical stress. The diacetylenic compounds disclosed herein require mild conditions for the ordering of the compounds in solution. With respect to diacetylenic compounds of the present invention that include an ammonium moiety the use of high temperatures and high intensity probe sonication is not required. Additionally, the diacetylenic compounds disclosed herein allow for the incorporation of large excesses of unpolymerizable monomer while still forming a stable, polymerizable solution. The diacetylenic compounds disclosed herein can be synthesized in a rapid high-yielding fashion, including high-throughput methods of synthesis. The presence of functionality in the backbones of the diacetylenic compounds disclosed herein, such as heteroatoms for example, provides for the possibility of easy structural elaboration in order to meet the requirements of a given sensing application. The diacetylenic compounds disclosed herein can be polymerized into the desired polydiacetylene backbone containing network by adding the diacetylene to a suitable solvent, such as water for example, heating or sonicating the mixture, and then irradiating the solution with ultraviolet light, typically at a wavelength of 254 nm. Upon polymerization the solution undergoes a color change to bluish-purple.

EXAMPLES

The present invention should not be considered limited to the particular examples described below, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. All parts, percentages, ratios, etc. in the examples and the rest of the specification are by weight unless indicated otherwise. All solvents and reagents without a named supplier were purchased from Aldrich Chemical; Milwaukee, Wis. Water was purified by the use of a UV Milli-Q water purifier with a resistivity of 18.2 Mohms/cm (Millipore Corp., Bedford, Mass.).

Table of Abbreviations

| Abbreviation or Trade Name | Description |
| --- | --- |
| 11-Bromo-1-undecanol | $Br(CH_2)_{11}OH$ Commercially available from Aldrich Chemical; Milwaukee, WI |
| 11-Bromoundecanoic acid | $Br(CH_2)_{10}C(O)OH$ Commercially available from Aldrich Chemical; Milwaukee, WI |
| TBDMSCl | Tert-butyldimethylsilyl chloride Commercially available from Aldrich Chemical; Milwaukee, WI |
| Diyne-1 | Bis(trimethylsilyl)butadiyne commercially available from Gelest; Tullytown, PA |
| THF | Tetrahydrofuran |
| 1-Bromododecane | $Br(CH_2)_{11}CH_3$ Commercially available from Aldrich Chemical; Milwaukee, WI |
| TBAF | Tetrabutylammonium fluoride Commercially available from Aldrich Chemical; Milwaukee, WI |
| HMPA | Hexamethylphosphoramide Commercially vailable from Aldrich Chemical; Milwaukee, WI |
| 1-Bromohexadecane | $Br(CH_2)_{15}CH_3$ Commercially available from Aldrich Chemical; Milwaukee, WI |
| Methanesulfonyl chloride | Commercially available from Aldrich Chemical; Milwaukee, WI |

-continued

Table of Abbreviations

| Abbreviation or Trade Name | Description |
| --- | --- |
| $CH_2Cl_2$ | Dichloromethane |
| DMF | Dimethylformamide |
| oxalyl chloride | ClCOCOCl commercially available from Aldrich Chemical, Milwaukee, WI |
| PDC | Pyridinium dichromate, commercially available from Aldrich Chemical, Milwaukee, WI |
| DMAP | 4-(dimethylamino)pyridine, commercially available from Aldrich Chemical, Milwaukee, WI |
| KAPA | Potassium 3-aminopropylamide prepared according to Abrams, S. R.; Shaw, A. C. Organic Syntheses, 1988, 66, 127-131. |

Example 1

Preparation of $CH_3(CH_2)_{10}CH_2C \equiv C-C \equiv C(CH_2)_{11}NR_3X$

Step 1: Preparation of $Br(CH_2)_{11}OSi(Me_2(CMe_3))$

In a glass reaction vessel, a solution of 3.0 grams (12 mmol) 11-Bromo-1-undecanol in 40 milliliters $CH_2Cl_2$ was prepared and to this was added 2.7 grams (18 mmol) TBDMSCl and 1.2 grams (18 mmol) imidazole. The resulting mixture was stirred at room temperature for 18 h, and the reaction was worked up using dichloromethane and brine. The dichloromethane layer was dried ($MgSO_4$), filtered, and concentrated to yield 4.5 grams of $Br(CH_2)_{11}OSi(Me_2(CMe_3))$.

Step 2: Preparation of $HC \equiv C-C \equiv C(CH_2)_{11}OSi(Me_2(CMe_3))$

In a glass reaction vessel, 710 milligrams (3.6 mmol) Diyne-1 was dissolved in 15 milliliters THF and cooled to −78° C. To this stirred solution was added 1 equivalent of methyl lithium (as complex with lithium bromide, 1.5 molar solution in $Et_2O$). The mixture was stirred for 30 minutes and added via cannula to a −15° C. solution of 1.47 grams (4.0 mmol) $Br(CH_2)_{11}OSi(Me_2(CMe_3))$ in 8 milliliters HMPA and 16 milliliters THF. The resulting mixture was worked up using pentane and brine. The pentane layer was dried ($MgSO_4$), filtered, and concentrated. To the resulting solid was added 3.6 milliliters TBAF (1 molar solution in THF) dissolved in 35 milliliters THF and 1 milliliters water. The solution was filtered and concentrated under vacuum to provide a crude solid. This material was purified using column chromatography eluting with 3% by volume of ethyl acetate in hexanes to yield 510 milligrams $HC \equiv C-C \equiv C(CH_2)_{11}OSi(Me_2(CMe_3))$.

Step 3: Preparation of $CH_3(CH_2)_{10}CH_2C \equiv C-C \equiv C(CH_2)_{11} OSi(Me_2(CMe_3))$ In a glass reaction vessel, 1.31 grams (3.9 mmol) $HC \equiv C-C \equiv C(CH_2)_{11}OSi(Me_2(CMe_3))$ prepared in Step 2, was dissolved in 20 milliliters THF and cooled to −78° C. To this stirred solution was dropwise added a solution of 2.8 milliliters n-butyl lithium (1.6 molar solution in hexanes). This solution was added via cannula to a −15° C. solution 7 milliliters of HMPA and 1.02 grams (4.10 mmol) 1-Bromododecane in 25 milliliters THF. The resulting mixture was worked up using heptane and brine. The heptane layer was dried ($MgSO_4$), filtered and concentrated. This material was purified using column chromatography eluting with 10% by volume of dichloromethane in hexanes to yield 680 milligrams $CH_3(CH_2)_{10}CH_2C{\equiv}C{-}C{\equiv}C(CH_2)_{11}OSi(Me_2(CMe_3))$.

Step 4: Preparation of Compound 1A: $CH_3(CH_2)_{10}CH_2C{\equiv}C{-}C{\equiv}C(CH_2)_{11}NH_3Cl$ In a glass reaction vessel, 650 milligrams (1.3 mmol) $CH_3(CH_2)_{10}CH_2C{\equiv}C{-}C{\equiv}C(CH_2)_{11}OSi(Me_2(CMe_3))$ was dissolved in 6.5 milliliters THF. To this stirred solution was added 2.0 milliliters TBAF (1 molar solution in THF). After 1 h of stirring, the reaction mixture was filtered and concentrated to 520 milligrams of $CH_3(CH_2)_{10}CH_2C{\equiv}C{-}C{\equiv}C(CH_2)_{11}OH$ which was used without further purification. In a glass reaction vessel, the $CH_3(CH_2)_{10}CH_2C{\equiv}C{-}C{\equiv}C(CH_2)_{11}OH$ was dissolved in 6.5 milliliters $CH_2Cl_2$ and 150 µL (2.0 mmol) methanesulfonyl chloride and 360 µL (2.6 mmol) triethyl amine were added. The reaction was stirred for 2 h and worked up using $CH_2Cl_2$ and brine. The $CH_2Cl_2$ layer was dried ($MgSO_4$), filtered, and concentrated to 680 milligrams of $CH_3(CH_2)_{10}CH_2C{\equiv}C{-}C{\equiv}C(CH_2)_{11}OS(O_2)CH_3$ which was used without further purification. In a glass reaction vessel, the $CH_3(CH_2)_{10}CH_2C{\equiv}C{-}C{\equiv}C(CH_2)_{11}OS(O_2)CH_3$ was dissolved in 6.5 milliliters DMF and 570 milligrams (8.8 mmol) sodium azide was added. The reaction was stirred for 20 h and worked up using pentane and brine. The pentane layer was dried ($MgSO_4$), filtered and concentrated. This material was purified using column chromatography eluting with 9% dichloromethane in hexanes to yield 260 milligrams of $CH_3(CH_2)_{10}CH_2C{\equiv}C{-}C{\equiv}C(CH_2)_{11}N_3$. In a glass reaction vessel, the $CH_3(CH_2)_{10}CH_2C{\equiv}C{-}C{\equiv}C(CH_2)_{11}N_3$ was dissolved in 10 milliliters THF and 0.5 milliliters water and 330 milligrams (1.3 mmol) triphenyl phosphine was added. After 20 h of stirring, hydrogen chloride gas was bubbled through the mixture for 30 seconds. The resulting solid was filtered and washed with diethyl ether to yield 190 milligrams $CH_3(CH_2)_{10}CH_2C{\equiv}C{-}C{\equiv}C(CH_2)_{11}NH_3Cl$.

Step 5: Preparation of Compound 1B: $CH_3(CH_2)_{10}CH_2C{\equiv}C{-}C{\equiv}C(CH_2)_{11}NMe_3I$ In a glass reaction vessel, 55 milligrams (0.13 mmol) $CH_3(CH_2)_{10}CH_2C{\equiv}C{-}C{\equiv}C(CH_2)_{11}NH_3Cl$ was dissolved in 5 milliliters acetonitrile and 100 µL (1.6 mmol) methyl iodide and 170 milligrams (1.6 mmol) sodium carbonate. The solution was stirred at room temperature for 20 h and filtered to yield 65 milligrams $CH_3(CH_2)_{10}CH_2C{\equiv}C{-}C{\equiv}C(CH_2)_{11}NMe_3I$.

Step 6: Preparation of Compound 1C: $CH_3(CH_2)_{10}CH_2C{\equiv}C{-}C{\equiv}C(CH_2)_{11}NMe_3Cl$ A sample of Compound 1B was converted to Compound 1C by passing it through a Dowex anion exchange resin with sodium chloride solution.

Example 2

Preparation of $CH_3(CH_2)_{14}CH_2C{\equiv}C{-}C{\equiv}C(CH_2)_{11}NR_3X$

Step 1: Preparation of $Br(CH_2)_{11}OSi(Me_2(CMe_3))$

The same procedure described in Example 1 Step 1 was followed.

Step 2: Preparation of $HC{\equiv}C{-}C{\equiv}C(CH_2)_{11}OSi(Me_2(CMe_3))$

The same procedure described in Example 1 Step 2 was followed.

Step 3: Preparation of $CH_3(CH_2)_{14}CH_2C{\equiv}C{-}C{\equiv}C(CH_2)_{11}OSi(Me_2(CMe_3))$ The same procedure described in Example 1 Step 3 was followed with the exception that 1-Bromohexadecane was used instead of 1-Bromododecane.

Step 4: Preparation of Compound 2A: $CH_3(CH_2)_{14}CH_2C{\equiv}C{-}C{\equiv}C(CH_2)_{11}NH_3Cl$ The same procedure described in Example 1 Step 4 was followed.

Step 5: Preparation of Compound 2B: $CH_3(CH_2)_{14}CH_2C{\equiv}C{-}C{\equiv}C(CH_2)_{11}NMe_3I$ The same procedure described in Example 1 Step 5 was followed.

Step 6: Preparation of Compound 2C: $CH_3(CH_2)_{14}CH_2C{\equiv}C{-}C{\equiv}C(CH_2)_{11}NMe_3Cl$ The same procedure described in Example 1 Step 6 was followed.

Example 3

Preparation of $CH_3(CH_2)_{10}C(O)OCH_2C{\equiv}C{-}C{\equiv}CCH_2OC(O)(CH_2)_{10}NH_3Cl$ Step 1: Preparation of $HOCH_2C{\equiv}C{-}C{\equiv}CCH_2OH$ Oxidative coupling of 3-Propyn-1-ol ($HOCH_2C{\equiv}CH$) was carried out in a glass reaction vessel by dissolving 122 grams (2.26 mol) 2-Propyn-1-ol in 70 milliliters pyridine and adding 11.1 grams (112 mmol) CuCl followed by the addition of 220 milliliters methyl alcohol. The reaction was stirred for 48 h in the presence of oxygen. The reaction was worked up using concentrated HCl and ethyl acetate. The ethyl acetate layer was dried ($MgSO_4$), filtered and concentrated to yield 61 grams $HOCH_2C{\equiv}C{-}C{\equiv}CCH_2OH$.

Step 2: Preparation of $N_3(CH_2)_{10}C(O)Cl$

In a glass reaction vessel, 10.6 grams (40 mmol) of 11-Bromoundecanoic acid was dissolved in 225 milliliters DMF and 26 grams (400 mmol) sodium azide was added. The resulting stirred mixture was heated to 80° C. for 16h, and then the reaction mixture was worked up with ether and brine. The ether layer was dried ($MgSO_4$), filtered, and concentrated to 9.5 grams of $N_3(CH_2)_{10}C(O)OH$ as a pale yellow oil which was used without purification. In a glass reaction vessel, the $N_3(CH_2)_{10}C(O)OH$ was dissolved in 120 milliliters benzene and 12.7 grams (100 mmol) oxalyl chloride was added. The reaction was allowed to stir for 20 h, at which time the volatiles were removed in vacuo. The resulting residue was dissolved in pentane and filtered in a nitrogen atmosphere to remove solids. Concentration of the filtrate afforded $N_3(CH_2)_{10}C(O)Cl$ as a clear, yellow oil.

Step 3: Preparation of $CH_3(CH_2)_{10}C(O)OCH_2C{\equiv}C{-}C{\equiv}CCH_2OC(O)(CH_2)_{10}NH_3Cl$ In a glass reaction vessel, 400 milligrams (3.75 mmol) $HOCH_2C{\equiv}C{-}C{\equiv}CCH_2OH$ prepared in Step 1, was dissolved in a mixture of 25 milliliters THF and 1 milliliters pyridine. To this stirred solution was added 1.0 gram (4.1 mmol) $N_3(CH_2)_{10}C(O)Cl$ prepared in Step 2, and 950 µL (4.1 mmol) $CH_3(CH_2)_{10}C(O)Cl$. The resulting mixture was stirred for 3 h, concentrated, dissolved into hexanes and filtered to remove the salts. The filtrate was concentrated and purified using column chromatography eluting with 10% by volume of ethyl acetate in hexanes to yield 750 milligrams $CH_3(CH_2)_{10}C(O)OCH_2C{\equiv}C{-}C{\equiv}CCH_2OC(O)(CH_2)_{10}N_3$. In a glass reaction vessel, 280 milligrams (0.56 mmol) $CH_3(CH_2)_{10}C(O)OCH_2C{\equiv}C{-}C{\equiv}CCH_2OC(O)$ $(CH_2)_{10}N_3$ was dissolved in 1 milliliters water and 8 milliliters THF. To this solution, 350 milligrams (1.3 mmol) triphenylphosphine was added. After 20 h of stirring, hydrogen chloride gas was bubbled through the mixture for 30 seconds. The resulting solid was filtered and washed with diethyl ether to yield 150 milligrams $CH_3(CH_2)_{10}C(O)OCH_2C\equiv C—C\equiv CCH_2OC(O)(CH_2)_{10}NH_3Cl$.

Example 4

Preparation of $CH_3(CH_2)_{10}C(O)O(CH_2)_3C\equiv C—C\equiv C(CH_2)_3OC(O)(CH_2)_{10}NH_3Cl$ Step 1: Preparation of $HO(CH_2)_3C\equiv C—C\equiv C(CH_2)_3OH$ (also commercially available as 4,6-decadiyn-1,10-diol from GFS; Powell, Ohio)

The same procedure was followed as for Example 3 Step 1, except that 4-Pentyn-1-ol ($HO(CH_2)_3C\equiv CH$) was used instead of 2-Propyn-1-ol.

Step 2: Preparation of $N_3(CH_2)_{00}C(O)Cl$

The same procedure was followed as for Example 3 Step 2.

Step 3: Preparation of $CH_3(CH_2)_{10}C(O)O(CH_2)_3C\equiv C—C\equiv C(CH_2)_3OC(O)(CH_2)_{10}NH_3Cl$ The same procedure was followed as for Example 3 Step 3 except that $HO(CH_2)_3C\equiv C—C\equiv C(CH_2)_3OH$ (prepared in Step 1) was used instead of $HOCH_2C\equiv C—C\equiv CCH_2OH$.

Example 5

Preparation of $CH_3(CH_2)_{10}C(O)O(CH_2)_4C\equiv C—C\equiv C(CH_2)_4OC(O)(CH_2)_{10}NH_3Cl$ Step 1: Preparation of $HO(CH_2)_4C\equiv C—C\equiv C(CH_2)_4OH$ (Also commercially available from GFS Chemicals; Powell, Ohio as 5,7-dodecadiyn-1,12-diol).

The same procedure was followed as for Example 3 Step 1, except that 5-Hexyn-1-ol ($HO(CH_2)_4C\equiv CH$) was used instead of 3-Propyn-1-ol.

Step 2: Preparation of $N_3(CH_2)_{10}C(O)Cl$

The same procedure was followed as for Example 3 Step 2.

Step 3: Preparation of $CH_3(CH_2)_{10}C(O)O(CH_2)_4C\equiv C—C\equiv C(CH_2)_4OC(O)(CH_2)_{10}NH_3Cl$ The same procedure was followed as for Example 3 Step 3 except that $HO(CH_2)_4C\equiv C—C\equiv C(CH_2)_4OH$ (prepared in Step 1) was used instead of $HOCH_2C\equiv C—C\equiv CCH_2OH$.

Example 6

Preparation of $CH_3(CH_2)_{14}C(O)OCH_2C\equiv C—C\equiv CCH_2OC(O)(CH_2)_{10}NH_3Cl$ Step 1: Preparation of $HOCH_2C\equiv C—C\equiv CCH_2OH$ The same procedure was followed as for Example 3 Step 1.

Step 2: Preparation of $N_3(CH_2)_{10}C(O)Cl$

The same procedure was followed as for Example 3 Step 2.

Step 3: Preparation of $CH_3(CH_2)_{14}C(O)O(CH_2)_4C\equiv C—C\equiv C(CH_2)_4OC(O)(CH_2)_{10}NH_3Cl$ The same procedure was followed as for Example 3 Step 3 except that Hexadecanyl chloride was used instead of Dodecanyl chloride.

Example 7

Preparation of $CH_3(CH_2)_{14}C(O)O(CH_2)_3C\equiv C—C\equiv C(CH_2)_3OC(O)(CH_2)_{10}NH_3Cl$ Step 1: Preparation of $HO(CH_2)_3C\equiv C—C\equiv C(CH_2)_3OH$ The same procedure was followed as for Example 4 Step 1.

Step 2: Preparation of $N_3(CH_2)_{10}C(O)Cl$

The same procedure was followed as for Example 3 Step 2.

Step 3: Preparation of $CH_3(CH_2)_{14}C(O)O(CH_2)_3C\equiv C—C\equiv C(CH_2)_3OC(O)(CH_2)_{10}NH_3Cl$ The same procedure was followed as for Example 4 Step 3 except that Hexadecanyl chloride was used instead of Dodecanyl chloride.

Example 8

Preparation of $CH_3(CH_2)_{14}C(O)O(CH_2)_4C\equiv C—C\equiv C(CH_2)_4OC(O)(CH_2)_{10}NH_3Cl$ Step 1: Preparation of $HO(CH_2)_4C\equiv C—C\equiv C(CH_2)_4OH$ The same procedure was followed as for Example 5 Step 1.

Step 2: Preparation of $N_3(CH_2)_{10}C(O)Cl$

The same procedure was followed as for Example 3 Step 2.

Step 3: Preparation of $CH_3(CH_2)_{14}C(O)O(CH_2)_4C\equiv C—C\equiv C(CH_2)_4OC(O)(CH_2)_{10}NH_3Cl$ The same procedure was followed as for Example 5 Step 3 except that Hexadecanyl chloride was used instead of Dodecanyl chloride.

Example 9

Samples of 1.0 milliMolar concentration solutions of Compounds 1A, 1B, 1C, 2A, 2B, 2C in water were prepared in glass vessels, heated in a 70° C. oven for 30 minutes, bath sonicated in a Bronson Model #1510 bath sonicator (commercially available from VWR Scientific Products; West Chester, Pa.) for 30 minutes, filtered through a 0.45 micrometer syringe filter and placed in a 4° C. refrigerator for about 16 hours. The solutions were removed from the refrigerator and polymerized by stirring while irradiating beneath a 254 nanometer wavelength UV lamp (commercially available from VWR Scientific Products; West Chester, Pa.) at a distance of 3 centimeters for 10 minutes. Whether polymerization occurred upon irradiation and the presence or absence of a color change is noted in Table 1. The samples in which polymerization occurred and a color change was observed were heated to 70° C. for 15 seconds. The resulting color change is noted in Table 1.

TABLE 1

| Example Compound | Did polymerization occur | Color of polymerized solution | Color of polymerized solution after heating to 70° C. |
| --- | --- | --- | --- |
| 1A | Yes | Blue | Red |
| 1B | Yes | Purple | Red |
| 1C | No | NA | NA |
| 2A | Yes | Blue | Red |
| 2B | Yes | Purple | Red |
| 2C | No | NA | NA |

NA = Not applicable

Example 10

Samples of 1.0 milliMolar concentration solutions of the compounds prepared in Examples 3-8 in water were prepared in glass vessels, heated in a 70° C. oven for 30 minutes and placed in a 4° C. refrigerator for about 16 hours. The solutions were removed from the refrigerator and polymerized by stirring while irradiating beneath a 254 nanometer wavelength UV lamp (commercially available from VWR Scientific Products; West Chester, Pa.) at a distance of 3 centimeters for 10 minutes. The color change observed upon polymerization is noted in Table 2. The samples were heated to 70° C. for 15 seconds and the resulting color change is noted in Table 2. A third color transition was produced by heating the solutions to 90° C., and this color transition, if present is also noted in Table 2.

TABLE 2

| Compound Example Number | Color of polymerized solution | Color of polymerized solution after heating to 70° C. | Third transition color |
|---|---|---|---|
| 3 | Yellow | Orange | NA |
| 6 | Yellow | Orange | NA |
| 4 | Purple | Orange | Yellow |
| 7 | Purple | Orange | Yellow |
| 5 | Blue | Red | Orange |
| 8 | Blue | Red | Orange |

NA = Not applicable

Example 11

Samples of 1.0 milliMolar concentration solutions of Compound 2B prepared in Example 2 in water were prepared in a glass vessels, heated in a 70° C. oven for 30 minutes, bath sonicated in a Bronson Model #1510 bath sonicator (commercially available from VWR Scientific Products; West Chester, Pa.) for 30 minutes, filtered through a 0.45 micrometer syringe filter and placed in a 4° C. refrigerator for about 16 hours. The solutions were removed from the refrigerator and polymerized by stirring while irradiating beneath a 254 nanometer wavelength UV lamp at a distance of 3 centimeters for 10 minutes. Salts containing other anions were added to the solutions. The presence or absence of an observed color change is recorded in Table 3.

TABLE 3

| Anion | Color Change Observed? |
|---|---|
| $Cl^-$ | Yes |
| $Br^-$ | Yes |
| $CO_3^{2-}$ | Yes |
| $SO_4^{2-}$ | Yes |
| $N_3^-$ | Yes |
| $I^-$ | No |

Example 12

Preparation of $HO(O)C(CH_2)_3C\equiv C-C\equiv C(CH_2)_4O(O)C(CH_2)_{10}CH_3$

Step 1: Preparation of $HO(CH_2)_4C\equiv C-C\equiv C(CH_2)_4O(O)C(CH_2)_{10}CH_3$ In a glass reaction vessel, 600 milligrams of 5,7-dodecadiyn-1,12-diol ($HO(CH_2)_4C\equiv C-C\equiv C(CH_2)_4OH$), 0.275 milliliters of pyridine and 10 milliliters of THF were mixed. To this solution was added 676 milligrams of lauroyl chloride and the resulting mixture was stirred for 15 hours. The mixture was then diluted with diethyl ether and washed with 0.1 N HCl and brine. The organic layer was separated, dried over $MgSO_4$, filtered and the solvent was removed to yield a white solid. The solid was purified over silica gel (gradient from 25% to 50% ethyl acetate in hexanes by volume) to yield 570 milligrams of $HO(CH_2)_4C\equiv C-C\equiv C(CH_2)_4O(O)C(CH_2)_{10}CH_3$ as a white solid.

Step 2: Preparation of $HO(O)C(CH_2)_3C\equiv C-C\equiv C(CH_2)_4O(O)C(CH_2)_{10}CH_3$ In a glass reaction vessel, 377 milligrams of $HO(CH_2)_4C\equiv C-C\equiv C(CH_2)_4O(O)C(CH_2)_{10}CH_3$ prepared in Step 1 was dissolved in 3 milliliters of DMF and 1.32 grams of PDC was added. The resulting mixture was stirred for 8 hours, and then worked up with water and diethyl ether. The combined ether layers were dried over $MgSO_4$, filtered and the solvent was removed to yield a white solid. The solid was purified over silica gel eluting with 25/74/1 of ethyl acetate/hexanes/formic acid by volume to yield 0.21 grams of $HO(O)C(CH_2)_3C\equiv C-C\equiv C(CH_2)_4O(O)C(CH_2)_{10}CH_3$ as a white solid.

Examples 13-16

Preparation of $HO(O)C(CH_2)_{a-1}C\equiv C-C\equiv C(CH_2)_aO(O)C(CH_2)_bCH_3$

The same procedure described in Example 12 was followed using the diol and acid chloride in Step 1 shown in Table 4 to give the compounds with the general structure $HO(O)C(CH_2)_{a-1}C\equiv C-C\equiv C(CH_2)_aO(O)C(CH_2)_bCH_3$ (a and b are defined in Table 4).

TABLE 4

| Example | Diol, a value | Acid Chloride, b value |
|---|---|---|
| 13 | $HO(CH_2)_3C\equiv C-C\equiv C(CH_2)_3OH$, a = 3 | $CH_3(CH_2)_{14}C(O)Cl$, b = 14 |
| 14 | $HO(CH_2)_4C\equiv C-C\equiv C(CH_2)_4OH$, a = 4 | $CH_3(CH_2)_{12}C(O)Cl$, b = 12 |
| 15 | $HO(CH_2)_4C\equiv C-C\equiv C(CH_2)_4OH$, a = 4 | $CH_3(CH_2)_{14}C(O)Cl$, b = 14 |
| 16 | $HO(CH_2)_4C\equiv C-C\equiv C(CH_2)_4OH$, a = 4 | $CH_3(CH_2)_{16}C(O)Cl$, b = 16 |

Example 17

Preparation of $HO(O)C(CH_2)_2C(O)O(CH_2)_4C\equiv C-C\equiv C(CH_2)_4O(O)C(CH_2)_{12}CH_3$ Step 1: Preparation of $HO(CH_2)_4C\equiv C-C\equiv C(CH_2)_4O(O)C(CH_2)_{12}CH_3$ In a glass reaction vessel, 4.99 grams of 5,7-dodecadiyn-1,12-diol ($HO(CH_2)_4C\equiv C-C\equiv C(CH_2)_4OH$), 2.2 grams of pyridine and 50 milliliters of THF were mixed. To this solution was added 6.34 grams of myristol chloride and the resulting mixture was stirred for 15 hours. The mixture was then diluted with diethyl ether and washed with 0.1 N HCl and brine. The organic layer was separated, dried over $MgSO_4$, filtered and the solvent was removed to yield a white solid. The solid was purified over silica gel (15% by volume of ethyl acetate in dichloromethane to 100% ethyl acetate gradient) to yield 5.0 grams of $HO(CH_2)_4C\equiv C-C\equiv C(CH_2)_4O(O)C(CH_2)_{12}CH_3$ as a white solid.

Step 2: Preparation of HO(O)C(CH$_2$)$_2$C(O)O(CH$_2$)$_4$C≡C—C≡C(CH$_2$)$_4$O(O)C(CH$_2$)$_{12}$CH$_3$ In a sealable tube, 1.41 grams of HO(CH$_2$)$_3$C≡C—C≡C(CH$_2$)$_4$O(O)C(CH$_2$)$_{12}$CH$_3$ prepared in Step 1, 0.435 grams of succinic anhydride, 13 milliliters of toluene and 0.106 grams of DMAP were combined and the tube was sealed. The mixture was heated to 105° C. for 14.5 hours, the reaction was cooled to room temperature, 0.15 milliliters of water was added, the tube was resealed and again heated to 105° C. for 30 minutes. The mixture was then diluted with diethyl ether and washed with 0.1 N HCl and brine. The organic layer was separated, dried over MgSO$_4$, filtered and the solvent was removed to yield a white solid. The solid was purified over silica gel eluting with 10/89/1 of ethyl acetate/dichloromethane/formic acid by volume to yield 1.70 grams of HO(O)C(CH$_2$)$_2$C(O)O(CH$_2$)$_4$C≡C—C≡C(CH$_2$)$_4$O(O)C(CH$_2$)$_{12}$CH$_3$ as a white solid.

Examples 18-28

Preparation of HO(O)C(CH$_2$)$_2$C(O)O(CH$_2$)$_a$C≡C—C≡C(CH$_2$)$_a$O(O)C(CH$_2$)$_b$CH$_3$ The same procedure described in Example 17 was followed using the diol and acid chloride in Step 1 shown in Table 5 to give the compounds with the general structure HO(O)C(CH$_2$)$_2$C(O)O(CH$_2$)$_a$C≡C—C≡C(CH$_2$)$_a$O(O)C(CH$_2$)$_b$CH$_3$ (a and b are defined in Table 5).

TABLE 5

| Example | Diol, a value | Acid Chloride, b value |
|---|---|---|
| 18 | HO(CH$_2$)$_2$C≡C—C≡C(CH$_2$)$_2$OH, a = 2 | CH$_3$(CH$_2$)$_{10}$C(O)Cl, b = 10 |
| 19 | HO(CH$_2$)$_2$C≡C—C≡C(CH$_2$)$_2$OH, a = 2 | CH$_3$(CH$_2$)$_{12}$C(O)Cl, b = 12 |
| 20 | HO(CH$_2$)$_2$C≡C—C≡C(CH$_2$)$_2$OH, a = 2 | CH$_3$(CH$_2$)$_{14}$C(O)Cl, b = 14 |
| 21 | HO(CH$_2$)$_2$C≡C—C≡C(CH$_2$)$_2$OH, a = 2 | CH$_3$(CH$_2$)$_{16}$C(O)Cl, b = 16 |
| 22 | HO(CH$_2$)$_3$C≡C—C≡C(CH$_2$)$_3$OH, a = 3 | CH$_3$(CH$_2$)$_{10}$C(O)Cl, b = 10 |
| 23 | HO(CH$_2$)$_3$C≡C—C≡C(CH$_2$)$_3$OH, a = 3 | CH$_3$(CH$_2$)$_{12}$C(O)Cl, b = 12 |
| 24 | HO(CH$_2$)$_3$C≡C—C≡C(CH$_2$)$_3$OH, a = 3 | CH$_3$(CH$_2$)$_{14}$C(O)Cl, b = 14 |
| 25 | HO(CH$_2$)$_3$C≡C—C≡C(CH$_2$)$_3$OH, a = 3 | CH$_3$(CH$_2$)$_{16}$C(O)Cl, b = 16 |
| 26 | HO(CH$_2$)$_4$C≡C—C≡C(CH$_2$)$_4$OH, a = 4 | CH$_3$(CH$_2$)$_{10}$C(O)Cl, b = 10 |
| 27 | HO(CH$_2$)$_4$C≡C—C≡C(CH$_2$)$_4$OH, a = 4 | CH$_3$(CH$_2$)$_{14}$C(O)Cl, b = 14 |
| 28 | HO(CH$_2$)$_4$C≡C—C≡C(CH$_2$)$_4$OH, a = 4 | CH$_3$(CH$_2$)$_{16}$C(O)Cl, b = 16 |

Example 29

Preparation of HO(O)C(CH$_2$)$_2$C(O)O(CH$_2$)$_5$C≡C—C≡C(CH$_2$)$_5$O(O)C(CH$_2$)$_{10}$CH$_3$ Step 1: Preparation of HO(CH$_2$)$_5$C≡C—C≡C(CH$_2$)$_5$OH HO(CH$_2$)$_5$C≡CH was prepared by the KAPA-promoted isomerization of HOCH$_2$C≡C(CH$_2$)$_3$CH$_3$ (prepared according to Millar, J. G.; Oehlschlager, A. C. *J. Org. Chem.* 1984, 49, 2332-2338) or HO(CH$_2$)$_2$C≡C(CH$_2$)$_2$CH$_3$ (commercially available GFS Chemicals; Powell, Ohio). Oxidative coupling of HO(CH$_2$)$_5$C≡CH was carried out in a glass reaction vessel by dissolving 6.95 grams of HO(CH$_2$)$_5$C≡CH in pyridine/methanol (2.0 milliliters/6.2 milliliters) and adding 307 grams of CuCl followed by stirring in the presence of oxygen until all the staring material was consumed. The reaction mixture was worked up with diethyl ether and 4N HCl, the combined organic layers were dried over MgSO$_4$, filtered and concentrated. Recrystallization of the residue from 1/1 hexanes/tert-butyl methyl ether to yield 5.35 grams of HO(CH$_2$)$_5$C≡C—C≡C(CH$_2$)$_5$OH as a pink solid.

Step 2: Preparation of HO(CH$_2$)$_5$C≡C—C≡C(CH$_2$)$_5$O(O)C(CH$_2$)$_{10}$CH$_3$ The same procedure described in Example 17 Step 1 was followed except that instead of 5,7-dodecadiyn-1,12-diol the diol prepared in Step 1 above was used.

Step 3: Preparation of HO(O)C(CH$_2$)$_2$C(O)O(CH$_2$)$_5$C≡C—C≡C(CH$_2$)$_5$O(O)C(CH$_2$)$_{10}$CH$_3$ The same procedure described in Example 17 Step 2 was followed.

Examples 30-32

Preparation of HO(O)C(CH$_2$)$_2$C(O)O(CH$_2$)$_5$C≡C—C≡C(CH$_2$)$_5$O(O)C(CH$_2$)$_b$CH$_3$ The same procedure described in Example 29 was followed using the diol and acid chloride in Step 2 shown in Table 6 to give the compounds with the general structure HO(O)C(CH$_2$)$_2$C(O)O(CH$_2$)$_5$C≡C—C≡C(CH$_2$)$_5$O(O)C(CH$_2$)$_b$CH$_3$ (b is defined in Table 6).

TABLE 6

| Example | Diol | Acid Chloride, b value |
|---|---|---|
| 30 | HO(CH$_2$)$_5$C≡C—C≡C(CH$_2$)$_5$OH | CH$_3$(CH$_2$)$_{12}$C(O)Cl, b = 12 |
| 31 | HO(CH$_2$)$_5$C≡C—C≡C(CH$_2$)$_5$OH | CH$_3$(CH$_2$)$_{14}$C(O)Cl, b = 14 |
| 32 | HO(CH$_2$)$_5$C≡C—C≡C(CH$_2$)$_5$OH | CH$_3$(CH$_2$)$_{16}$C(O)Cl, b = 16 |

Examples 33-36

Preparation of HO(O)C(CH$_2$)$_2$C(O)O(CH$_2$)$_6$C≡C—C≡C(CH$_2$)$_6$O(O)C(CH$_2$)$_b$CH$_3$ The same procedure described in Example 29 Step 1 was followed to prepare the diol HO(CH$_2$)$_6$C≡C—C≡C(CH$_2$)$_6$OH starting from 1-heptyne. The remaining procedure for Example 29 was followed using the diol and acid chloride in Step 2 shown in Table 7 to give the compounds with the general structure HO(O)C(CH$_2$)$_2$C(O)O(CH$_2$)$_6$C≡C—C≡C(CH$_2$)$_6$O(O)C(CH$_2$)$_b$CH$_3$ (b is defined in Table 7).

TABLE 7

| Example | Diol | Acid Chloride, b value |
| --- | --- | --- |
| 33 | HO(CH$_2$)$_6$C≡C—C≡C(CH$_2$)$_6$OH | CH$_3$(CH$_2$)$_{10}$C(O)Cl, b = 10 |
| 34 | HO(CH$_2$)$_6$C≡C—C≡C(CH$_2$)$_6$OH | CH$_3$(CH$_2$)$_{12}$C(O)Cl, b = 12 |
| 35 | HO(CH$_2$)$_6$C≡C—C≡C(CH$_2$)$_6$OH | CH$_3$(CH$_2$)$_{14}$C(O)Cl, b = 14 |
| 36 | HO(CH$_2$)$_6$C≡C—C≡C(CH$_2$)$_6$OH | CH$_3$(CH$_2$)$_{16}$C(O)Cl, b = 16 |

Examples 37-39

Preparation of HO(O)C(CH$_2$)$_2$C(O)O(CH$_2$)$_7$C≡C—C≡C(CH$_2$)$_7$O(O)C(CH$_2$)$_b$CH$_3$ The same procedure described in Example 29 Step 1 was followed to prepare the diol HO(CH$_2$)$_7$C≡C—C≡C(CH$_2$)$_7$OH staring from 1-octyne. The remaining procedure for Example 29 was followed using the diol and acid chloride in Step 2 shown in Table 8 to give the compounds with the general structure HO(O)C(CH$_2$)$_2$C(O)O(CH$_2$)$_7$C≡C—C≡C(CH$_2$)$_7$O(O)C(CH$_2$)$_b$CH$_3$ (b is defined in Table 8).

TABLE 8

| Example | Diol | Acid Chloride |
| --- | --- | --- |
| 37 | HO(CH$_2$)$_7$C≡C—C≡C(CH$_2$)$_7$OH | CH$_3$(CH$_2$)$_{10}$C(O)Cl, b = 10 |
| 38 | HO(CH$_2$)$_7$C≡C—C≡C(CH$_2$)$_7$OH | CH$_3$(CH$_2$)$_{12}$C(O)Cl, b = 12 |
| 39 | HO(CH$_2$)$_7$C≡C—C≡C(CH$_2$)$_7$OH | CH$_3$(CH$_2$)$_{16}$C(O)Cl, b = 16 |

Examples 40-43

Preparation of HO(O)C(CH$_2$)$_2$C(O)O(CH$_2$)$_9$C≡C—C≡C(CH$_2$)$_9$O(O)C(CH$_2$)$_b$CH$_3$ The same procedure described in Example 29 Step 1 was followed to prepare the diol HO(CH$_2$)$_9$C≡C—C≡C(CH$_2$)$_9$OH starting from 1-decyne. The remaining procedure for Example 29 was followed using the diol and acid chloride in Step 2 shown in Table 9 to give the compounds with the general structure HO(O)C(CH$_2$)$_2$C(O)O(CH$_2$)$_9$C≡C—C≡C(CH$_2$)$_9$O(O)C(CH$_2$)$_b$CH$_3$ (b is defined in Table 9)

TABLE 9

| Example | Diol | Acid Chloride, b value |
| --- | --- | --- |
| 40 | HO(CH$_2$)$_9$C≡C—C≡C(CH$_2$)$_9$OH | CH$_3$(CH$_2$)$_{10}$C(O)Cl, b = 10 |
| 41 | HO(CH$_2$)$_9$C≡C—C≡C(CH$_2$)$_9$OH | CH$_3$(CH$_2$)$_{12}$C(O)Cl, b = 12 |
| 42 | HO(CH$_2$)$_9$C≡C—C≡C(CH$_2$)$_9$OH | CH$_3$(CH$_2$)$_{14}$C(O)Cl, b = 14 |
| 43 | HO(CH$_2$)$_9$C≡C—C≡C(CH$_2$)$_9$OH | CH$_3$(CH$_2$)$_{16}$C(O)Cl, b = 16 |

Example 44

Preparation of HO(O)C(CH$_2$)$_3$C(O)O(CH$_2$)$_4$C≡C—C≡C(CH$_2$)$_4$O(O)C(CH$_2$)$_{12}$CH$_3$ The same procedure described in Example 17 was followed except that in Step 2 glutaric anhydride was used in place of succinic anhydride.

Example 45

Preparation of HO(O)CHC≡CHC(O)O(CH$_2$)$_4$C≡C—C≡C(CH$_2$)$_4$O(O)C(CH$_2$)$_{14}$CH$_3$ The same procedure described in Example 17 was followed except that in Step 1 CH$_3$(CH$_2$)$_{14}$C(O)Cl was used instead of CH$_3$(CH$_2$)$_{12}$C(O)Cl and in Step 2 maleic anhydride was used in place of succinic anhydride.

Example 46

Preparation of HO(O)C(1,2-C$_6$H$_4$)C(O)O(CH$_2$)$_4$C≡C—C≡C(CH$_2$)$_4$O(O)C(CH$_2$)$_{12}$CH$_3$ The same procedure described in Example 17 was followed except that in Step 2 phthalic anhydride was used in place of succinic anhydride.

Example 47

Preparation of HO(O)C(CH$_2$)$_2$C(O)O(CH$_2$)$_4$C≡C—C≡C(CH$_2$)$_4$O(CH$_2$)$_{11}$CH$_3$ Step 1: Preparation of HO(CH$_2$)$_4$C≡C—C≡C(CH$_2$)$_4$O(CH$_2$)$_{11}$CH$_3$ In a glass reaction vessel, a suspension of 120 milligrams of sodium hydride was prepared in 10 milliliters dry DMF and 972 milligrams of 5,7-dodecadiyn-1,12-diol (HO(CH$_2$)$_4$C≡C—C≡C(CH$_2$)$_4$OH), was added. After stirring for 5 minutes 1.31 grams of CH$_3$(CH$_2$)$_{11}$Br was added and the resulting mixture was stirred for 15 hours. The mixture was then quenched by addition of saturated NH$_4$Cl solution and diluted with 100 milliliters of diethyl ether. The organic layer was separated and washed 3 times with brine, dried over MgSO$_4$, filtered and the solvent was removed to yield a yellow oil. The oil was purified over silica gel (25%-35% by volume of ethyl acetate in hexanes gradient) to yield 606 milligrams of HO(CH$_2$)$_4$C≡C—C≡C(CH$_2$)$_4$O(CH$_2$)$_{11}$CH$_3$ as a white solid.

Step 2: Preparation of HO(O)C(CH$_2$)$_2$C(O)O(CH$_2$)$_4$C≡C—C≡C(CH$_2$)$_4$O(CH$_2$)$_{11}$CH$_3$ In a sealable tube, 181 milligrams of HO(CH$_2$)$_4$C≡C—C≡C(CH$_2$)$_4$O(CH$_2$)$_{11}$CH$_3$ prepared in Step 1, 63 milligrams of succinic anhydride, 2 milliliters of toluene and 15 milligrams of DMAP were combined and the tube was sealed. The mixture was heated to 110° C. for 16 hours, the reaction was cooled to room temperature, 3 drops of water was added, the tube was resealed and again heated to 110° C. for 30 minutes. The mixture was then diluted with diethyl ether and washed with 0.1 N HCl and brine. The organic layer was separated, dried over MgSO$_4$, filtered and solvent was removed to yield a white solid. The solid was purified over silica gel eluting with 10/89/1 of ethyl acetate/dichloromethane/formic acid by volume to yield HO(O)C(CH$_2$)$_2$C(O)O(CH$_2$)$_4$C≡C—C≡C(CH$_2$)$_4$O(CH$_2$)$_{11}$CH$_3$ as a white solid.

Examples 48-52

Preparation of HO(O)C(CH$_2$)$_2$C(O)O(CH$_2$)$_a$C≡C—C≡C(CH$_2$)$_a$O(CH$_2$)$_b$CH$_3$ The same procedure described in Example 47 was followed using the diol and alkyl bromide in Step 1 shown in Table 10 to give the compounds with the general structure HO(O)C(CH$_2$)$_2$C(O)O(CH$_2$)$_a$C≡C—C≡C(CH$_2$)$_a$O(CH$_2$)$_b$CH$_3$ (a and b are defined in Table 10).

TABLE 10

| Example | Diol, a value | Alkyl Bromide, b value |
|---|---|---|
| 48 | HO(CH$_2$)$_2$C≡C—C≡C(CH$_2$)$_2$OH, a = 4 | CH$_3$(CH$_2$)$_b$Br, b = 13 |
| 49 | HO(CH$_2$)$_2$C≡C—C≡C(CH$_2$)$_2$OH, a = 4 | CH$_3$(CH$_2$)$_b$Br, b = 15 |
| 50 | HO(CH$_2$)$_2$C≡C—C≡C(CH$_2$)$_2$OH, a = 4 | CH$_3$(CH$_2$)$_b$Br, b = 17 |
| 51 | HO(CH$_2$)$_2$C≡C—C≡C(CH$_2$)$_2$OH, a = 5 | CH$_3$(CH$_2$)$_b$Br, b = 11 |
| 52 | HO(CH$_2$)$_3$C≡C—C≡C(CH$_2$)$_3$OH, a = 5 | CH$_3$(CH$_2$)$_b$Br, b = 13 |

Example 53

A sample of 10.1 milligrams of the compound prepared in Example 17 was placed in a glass vessel and suspended in 5 milliliters of isopropanol. The mixture was heated to boiling and 10 milliliters of 70° C. water was added. The resulting solution was boiled until the temperature reached 95° C. indicating the nearly all of the isopropanol had boiled off. The solution was cooled to room temperature and then to 4° C. for 16 hours. A 2 milliliter aliquot of the solution was exposed 254 nanometer light for 10 minutes, producing a dark blue color indicative that polymerization had occurred.

What is claimed is:

1. A polymerized composition comprising the polymerization reaction product of at least one compound of the formula

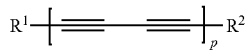

wherein R$^1$ is dodecyl or hexadecyl;
R$^2$ is,

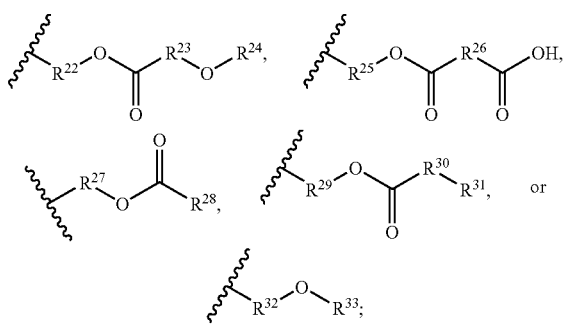

R$^{24}$, R$^{31}$ and R$^{33}$ are independently C$_1$-C$_{20}$ alkyl;
R$^{22}$, R$^{25}$, and R$^{32}$ are independently C$_1$-C$_{14}$ alkylene;
R$^{26}$ is C$_1$-C$_{14}$ alkylene, or C$_2$-C$_8$ alkenylene,
R$^{27}$, and R$^{29}$ are independently C$_1$-C$_{14}$ alkylene or (C$_1$-C$_{14}$ alkylene)-(C$_2$-C$_8$ arylene);
R$^{28}$ is C$_2$-C$_{30}$ alkynyl;
R$^{23}$ is C$_6$-C$_{13}$ arylene;
R$^{30}$ is C$_1$-C$_{14}$ alkylene;
p is 1-5;
and
wherein R$^1$ and R$^2$ are not the same.

2. The polymerized composition of claim 1, wherein R$^{24}$ is methyl, ethyl, propyl, butyl, pentyl, hexyl, heptyl, octyl, nonyl, or dodecyl.

3. The polymerized composition of claim 1, wherein R$^{33}$ is dodecyl, tetradecyl, hexadecyl, or octadecyl.

4. The polymerized composition of claim 1, wherein R$^{25}$ is independently ethylene, trimethylene, tetramethylene, pentamethylene, hexamethylene, heptamethylene, octamethylene, or nonamethylene.

5. The polymerized composition of claim 1, wherein R$^{22}$ is ethylene, trimethylene, or tetramethylene.

6. The polymerized composition of claim 1, wherein R$^{32}$ is ethylene, trimethylene, tetramethylene, pentamethylene, or hexamethylene.

7. The polymerized composition of claim 1, wherein R$^{26}$ is ethylene, trimethylene, ethenylene, or phenylene.

8. The polymerized composition of claim 1, wherein R$^{31}$ is C$_1$-C$_{14}$ alkyl.

9. The polymerized composition of claim 8, wherein R$^{31}$ is butyl, pentyl or hexyl.

10. The polymerized composition of claim 1, wherein R$^{27}$ and R$^{29}$ are independently methylene, ethylene, trimethylene, tetramethylene, —C(CH$_3$)$_2$—, —CH((CH$_2$)$_{1-4}$CH$_3$)—, or —CH$_2$-phenylene.

11. The polymerized composition of claim 1, wherein R$^{28}$ is C$_2$-C$_{30}$ alkynyl having at least two carbon-carbon triple bonds.

12. The polymerized composition of claim 11, wherein R$^{28}$ is (CH$_2$)$_8$—C≡C—C≡C—(CH$_2$)$_9$CH$_3$, or —(CH$_2$)$_8$—C≡C—C≡C—(CH$_2$)$_{11}$CH$_3$.

13. The polymerized composition of claim 1, wherein R$^{23}$ is phenylene.

14. The polymerized composition of claim 1, wherein p is 1 or 2.

15. The polymerized composition of claim 1, wherein the composition has a color in the visible spectrum less than 570 nm.

16. The polymerized composition of claim 1, wherein the composition has a color in the visible spectrum between 570 nm and 600 nm.

17. The polymerized composition of claim 1, wherein the composition has an observed color in the visible spectrum greater than 600 nm.

18. A polymerized composition comprising the polymerization reaction product of at least one compound of the formula

wherein $R^1$ is

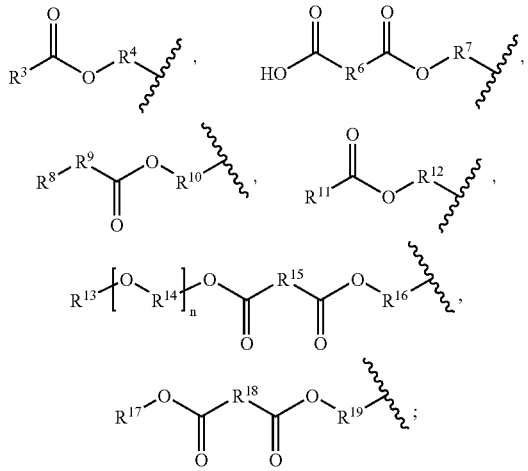

$R^2$ is $(C_7\text{-}C_{18}$ alkyl$)$—$NR^{35}_3X$, wherein $R^{35}$ is H and each X is independently $F^-$, $Br^-$, $Cl^-$, $I^-$, $OH^-$, $N_3^-$, $HCO_3^-$, or $CN^-$;

$R^3$, $R^8$ and $R^{13}$, are independently $C_1\text{-}C_{20}$ alkyl;

$R^4$, $R^7$, $R^{14}$, $R^{16}$, and $R^{19}$, are independently $C_1\text{-}C_{14}$ alkylene;

$R^6$, $R^{15}$, and $R^{18}$ are independently $C_1\text{-}C_{14}$ alkylene, or $C_2\text{-}C_8$ alkenylene, or $C_6\text{-}C_{13}$ arylene;

$R^9$ is $C_1\text{-}C_{14}$ alkylene;

$R^{10}$ and $R^{12}$, are independently $C_1\text{-}C_{14}$ alkylene or $(C_1\text{-}C_{14}$ alkylene$)$ —$(C_2\text{-}C8$ arylene$)$;

$R^{11}$ is independently $C_2\text{-}C_{30}$ alkynyl;

$R^{17}$ is an ester activating group;

p is 1-5;

n is 1-20; and wherein $R^1$ and $R^2$ are not the same.

19. The polymerized composition of claim 18, wherein $R^2$ is —$(CH_2)_{11}$—$NH_3X$, —$(CH_2)_{11}$—$N(CH_3)_3X$, —$(CH_2)_{15}$—$N(CH_3)_3X$, or —$(CH_2)_{15}$—$NH_3X$, wherein each X is independently $Cl^-$, or $I^-$.

20. The polymerized composition of claim 18, wherein $R^2$ is $(C_1\text{-}C_{18}$ alkyl$)$—$NR^{35}_3X$, wherein $R^{35}$ is $C_1\text{-}C_4$ alkyl and each X is independently $F^-$, $Br^-$, $Cl^-$, $I^-$, $OH^-$, $N_3^-$, $HCO_3^-$, or $CN^-$.

21. A method of making a polymerized composition of claim 1, the method comprising:
mixing one or more compounds of claim 1 in water;
processing the aqueous mixture to cause self-assembly of the one or more compounds; and
polymerizing the one or more compounds.

22. The method of claim 21 wherein processing the aqueous mixture to cause self-assembly comprises heating or sonicating the mixture, and polymerizing comprises irradiating the mixture with actinic radiation.

23. A polymerized composition comprising the polymerization reaction product of at least one compound of the formula

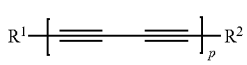

wherein $R^1$ is

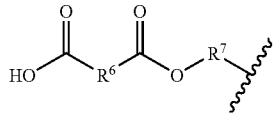

wherein $R^7$ is ethylene, trimethylene, tetramethylene, pentamethylene, hexamethylene, heptamethylene, octamethylene, or nonamethylene, and $R^6$ is ethylene, trimethylene, ethenylene, or phenylene; and wherein $R^2$ is

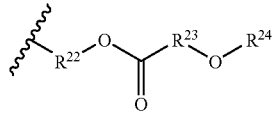

wherein $R^{22}$ is ethylene, trimethylene, or tetramethylene, $R^{23}$ is phenylene, and $R^{24}$ is methyl, ethyl, propyl, butyl, pentyl, hexyl, heptyl, octyl, nonyl, or dodecyl; and wherein p is 1.

24. A polymerized composition comprising the polymerization reaction product of at least one compound of the formula

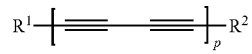

wherein $R^1$ is

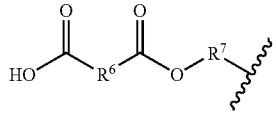

wherein $R^7$ is ethylene, trimethylene, tetramethylene, pentamethylene, hexamethylene, heptamethylene, octamethylene, or nonamethylene, and $R^6$ is ethylene, trimethylene, ethenylene, or phenylene; and wherein $R^2$ is

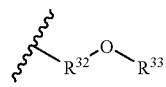

wherein $R^{32}$ is ethylene, trimethylene, tetramethylene, pentamethylene, or hexamethylene and $R^{33}$ is dodecyl, tetradecyl, hexadecyl, or octadecyl; and wherein p is 1.

25. A polymerized composition comprising the polymerization reaction product of at least one compound of the formula

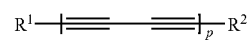

wherein $R^1$ is

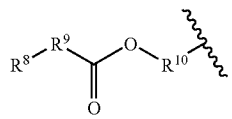

wherein $R^8$ is butyl, pentyl or hexyl, $R^9$ is methylene, and $R^{10}$ is methylene, ethylene, trimethylene, tetramethylene, —C(CH$_3$)$_2$—, —CH((CH$_2$)$_{1-4}$CH$_3$)—, or —CH$_2$-phenylene; and wherein $R^2$ is

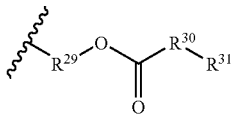

wherein $R^{29}$ is methylene, ethylene, trimethylene, tetramethylene, —C(CH$_3$)$_2$—, —CH((CH$_2$)$_{1-4}$CH$_3$)—, or —CH$_2$-phenylene, $R^{30}$ is methylene, and $R^{31}$ is butyl, pentyl or hexyl; and wherein p is 1.

26. A polymerized composition comprising the polymerization reaction product of at least one compound of the formula

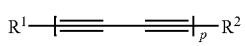

wherein $R^1$ is

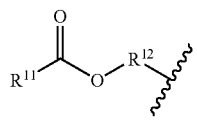

wherein $R^{11}$ is C$_1$-C$_{20}$ alkynyl having at least two carbon-carbon triple bonds, and $R^{12}$ is methylene, ethylene, trimethylene, tetramethylene, —C(CH$_3$)$_2$—, —CH((CH$_2$)$_{1-4}$CH$_3$)—, or —CH$_2$-phenylene; and wherein $R^2$ is

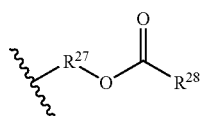

wherein $R^{27}$ is methylene, ethylene, trimethylene, tetramethylene, —C(CH$_3$)$_2$—, —CH((CH$_2$)$_{1-4}$CH$_3$)—, or —CH$_2$-phenylene, and $R^{28}$ is C$_1$-C$_{20}$ alkynyl having at least two carbon-carbon triple bonds; and wherein p is 1.

27. A polymerized composition comprising the polymerization reaction product of at least one compound of the formula

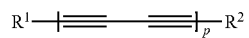

wherein $R^1$ is

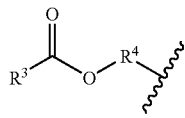

wherein $R^3$ is undecyl or pentadecyl, and $R^4$ is methylene, ethylene, or tetramethylene; and wherein $R^2$ is

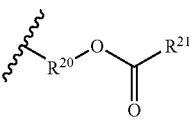

wherein $R^{20}$ is methylene, trimethylene, or tetramethylene, and $R^{21}$ is

—(CH$_2$)$_{10}$—NH$_3$X,  —(CH$_2$)$_{10}$—N(CH$_3$)$_3$X, (CH$_2$)$_{14}$—N(CH$_3$)$_3$X, or

—(CH$_2$)$_{14}$—NH$_3$X, wherein each X is independently Cl$^-$ or I$^-$; and wherein p is 1.

28. A polymerized composition comprising the polymerization reaction product of at least one compound of the formula

wherein $R^1$ is

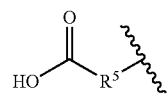

wherein $R^5$ is ethylene or trimethylene; and wherein $R^2$ is

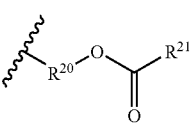

wherein $R^{20}$ is trimethylene or tetramethylene, and $R^{21}$ is undecyl, tridecyl, pentadecyl, or heptadecyl; and wherein p is 1.

29. A polymerized composition comprising the polymerization reaction product of at least one compound of the formula $$R^1-[\equiv\quad\equiv]_p-R^2$$

wherein $R^1$ is

[structure: HO-C(=O)-R^6-C(=O)-O-R^7-]

wherein $R^7$ is ethylene, trimethylene, tetramethylene, pentamethylene, hexamethylene, heptamethylene, octamethylene, or nonamethylene, and $R^6$ is ethylene, trimethylene, ethenylene, or phenylene; and
wherein $R^2$ is

[structure: -R^20-O-C(=O)-R^21]

wherein $R^{20}$ is ethylene, trimethylene, tetramethylene, pentamethylene, hexamethylene, heptamethylene, octamethylene, or nonamethylene, and wherein $R^{21}$ is undecyl, tridecyl, pentadecyl, heptadecyl; and
wherein p is 1.

30. A polymerized composition comprising the polymerization reaction product of at least one compound of the formula $$R^1-[\equiv\quad\equiv]_p-R^2$$

wherein $R^1$ is

[structure: R^13-[O-R^14]_n-O-C(=O)-R^15-C(=O)-O-R^16-]

wherein $R^{16}$ is ethylene, trimethylene, tetramethylene, pentamethylene, hexamethylene, heptamethylene, octamethylene, or nonamethylene, $R^{15}$ is ethylene, trimethylene, ethenylene, or phenylene, $R^{14}$ is ethylene, $R^{13}$ is methyl; and
wherein $R^2$ is

[structure: -R^20-O-C(=O)-R^21]

wherein $R^{20}$ is methylene, trimethylene, or tetramethylene, and $R^{21}$ is tridecyl; and
wherein p is 1 and n is 9-11.

31. A polymerized composition comprising the polymerization reaction product of at least one compound of the formula $$R^1-[\equiv\quad\equiv]_p-R^2$$

wherein $R^1$ is

[structure: R^17-O-C(=O)-R^18-C(=O)-O-R^19-]

wherein $R^{17}$ is 2,5-dioxo-1-pyrrolidinyl, $R^{18}$ is ethylene, trimethylene, ethenylene, or phenylene $R^{19}$ is ethylene, trimethylene, tetramethylene, pentamethylene, hexamethylene, heptamethylene, octamethylene, or nonamethylene; and
wherein $R^2$ is

[structure: -R^20-O-C(=O)-R^21]

wherein $R^{20}$ is methylene, trimethylene, or tetramethylene, and $R^{21}$ is tridecyl; and
wherein p is 1.

* * * * *

UNITED STATES PATENT AND TRADEMARK OFFICE
CERTIFICATE OF CORRECTION

PATENT NO. : 7,816,473 B2
APPLICATION NO. : 11/177643
DATED : October 19, 2010
INVENTOR(S) : Hays et al.

It is certified that error appears in the above-identified patent and that said Letters Patent is hereby corrected as shown below:

Column 4,
Line 58, delete "$R^{13}R^{24}$" and insert in place thereof --$R^{13}$, $R^{24}$--.

Column 7,
Line 8, delete "Br_," and insert in place thereof --Br ,--.

Column 8,
Line 10, delete "C=C" and insert in place thereof --C≡C--.

Column 9,
In Scheme I, formula III, delete "$N^+(CH_3)Cl$" and insert in place thereof --$N^+H_3Cl$--.
In Scheme I, delete "III" and insert in place thereof --II--.

Column 10,
In Scheme I, formula I, delete "$N^+(CH_3)Cl$" and insert in place thereof --$N^+(CH_3)_3Cl$--.

Column 15,
Line 62, delete "vailable" and insert in place thereof --available--.

Column 19,
Line 21, delete "$(CH_2)_{00}$" and insert in place thereof --$(CH_2)_{10}$--.

Column 24,
Line 58, delete "C=C" and insert in place thereof --C≡C--.

Column 25,
Line 49, delete "C=C" and insert in place thereof --C≡C--.
Line 55, delete "Table 9)" and insert in place thereof --Table 9).--.

Signed and Sealed this
Twenty-ninth Day of November, 2011

David J. Kappos
*Director of the United States Patent and Trademark Office*

CERTIFICATE OF CORRECTION (continued)
U.S. Pat. No. 7,816,473 B2

Column 26,
Line 12, delete "CHC≡CHC" and insert in place thereof --CHC=CHC--.

Column 29,
Line 21, before the chemical structure shown insert --or--.
Line 34, delete "($C_2$-C8" and insert in place thereof --($C_2$-$C_8$--.

Column 32,
Line 33, delete "$(CH_2)_{14}$" and insert in place thereof -- –$(CH_2)_{14}$--.